(12) United States Patent
Liotta et al.

(10) Patent No.: US 6,969,614 B1
(45) Date of Patent: Nov. 29, 2005

(54) METHODS FOR THE ISOLATION AND ANALYSIS OF CELLULAR PROTEIN CONTENT

(75) Inventors: Lance A. Liotta, Bethesda, MD (US); Nicole Simone, Lawrenceville, NJ (US); Michael Emmert-Buck, Silver Spring, MD (US); Emmanuel F. Petricoin III, Dunkirk, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/913,667

(22) PCT Filed: Feb. 16, 2000

(86) PCT No.: PCT/US00/04023

§ 371 (c)(1),
(2), (4) Date: Jan. 22, 2002

(87) PCT Pub. No.: WO00/49410

PCT Pub. Date: Aug. 24, 2000

Related U.S. Application Data

(60) Provisional application No. 60/120,288, filed on Feb. 16, 1999.

(51) Int. Cl.[7] .......................... G01N 1/30; G01N 33/53; G01N 21/00; G01N 21/75; G01N 1/18

(52) U.S. Cl. ...................... 436/177; 436/164; 436/178; 435/6; 435/4; 435/7.1; 435/7.9; 435/40.5; 435/40.52

(58) Field of Search .............................. 435/6, 4, 100, 435/7.1, 7.9, 40.5, 40.52; 436/177, 164, 178

(56) References Cited

U.S. PATENT DOCUMENTS

| | | | |
|---|---|---|---|
| 4,976,957 A | | 12/1990 | Bogoch |
| 5,843,644 A | * | 12/1998 | Liotta et al. .................. 435/6 |
| 5,843,657 A | | 12/1998 | Liotta et al. |
| 6,010,888 A | * | 1/2000 | Liotta et al. ................ 435/100 |
| 6,251,467 B1 | * | 6/2001 | Liotta et al. ............... 427/2.11 |
| 6,251,615 B1 | * | 6/2001 | Bonner et al. ............. 428/346 |
| 6,569,639 B2 | * | 5/2003 | Liotta et al. .............. 435/40.5 |
| 6,602,661 B1 | * | 8/2003 | Knezevic et al. .............. 435/6 |
| 6,680,203 B2 | * | 1/2004 | Dasseux et al. ............. 436/86 |
| 6,699,721 B1 | * | 3/2004 | Peterson et al. ........... 436/176 |
| 6,790,636 B1 | * | 9/2004 | Star et al. ................. 435/40.5 |

FOREIGN PATENT DOCUMENTS

| | | | | |
|---|---|---|---|---|
| JP | 61 275221 A | | 12/1986 | |
| WO | WO 99/44062 | * | 9/1999 | .......... G01N 33/50 |
| WO | WO 99/44063 | * | 9/1999 | .......... G01N 33/50 |

OTHER PUBLICATIONS

Suarez-Quian et al, Bio Techniques, Feb. 1999, 26:328-335.*
Olsen et al, Neuroendocrinology, 1989, 50/4:392-399 Abstract only.*
Dolter et al, BioTechniques, Jun. 2001, 30/6:1358-1361 Abstract only.*
Lindeman et al, Diagn. Mol. Pathol., Dec. 2002, 11/4:187-192 Abstract only.*
Kobayashi et al., J. Vet. Med. Sci., 2003, 65/8:917-919.*
Ornetein et al, Clinical Cancer Research, Feb. 2000, 6:353-356.*
Evans et al, Reprod. Biol. Endocrinol. 2003, 1/1:54.*
Trogan et al, PNAS USA, Feb. 2002, 99/4:2243-2239.*
Sluka et al, Biology of Reproduction, 2002, 67:820-828.*
Nakazono et al, The Plant Cell, Mar. 2003, 15/3:583-596.*
Heinmoller et al, Pathol. Res. Pract., 2003, 199/6:363-371 Abstract only.*
Tsukamoto et al, Cancer Sci., Dec. 2003, 94/12:1046-1051.*
Casanova et al, BioTechniques, Feb. 2002, 32/2:242-248.*
Burbach et al, J. Neuroscience Methods, 2004, 138:141-148.*
Luo et al, Nature Medicine, Jan. 1999, 5/1:117-122.*
Bartorfi et al, Gynecological Oncology, 2003, 88:424-428.*
Sacci et al, Molecular and Biochemical Parasitology, 2002, 119:285-289.*

(Continued)

*Primary Examiner*—N. M. Minnifield
(74) *Attorney, Agent, or Firm*—Klarquist Sparkman LLP

(57) ABSTRACT

The present invention describes devices and methods for performing protein analysis on laser capture microdissected cells, which permits proteomic analysis on cells of different populations. Particular disclosed examples are analysis of normal versus malignant cells, or a comparison of differential protein expression in cells that are progressing from normal to malignant. The protein content of the microdissected cells may be analyzed using techniques such as immunoassays, 1D and 2D gel electrophoresis characterization, Western blotting, liquid chromatography quadrapole ion trap electrospray (LCQ-MS), Matrix Assisted Laser Desorption Ionization/Time of Flight (MALDI/TOF), and Surface Enhanced Laser Desorption Ionization Spectroscopy (SELDI). In addition to permitting direct comparison of qualitative and quantitative protein content of tumor cells and normal cells from the same tissue sample, the methods also allow for investigation of protein characteristics of tumor cells, such as binding ability and amino acid sequence, and differential expression of proteins in particular cell populations in response to drug treatment. The present methods also provide, through the use of protein fingerprinting, a rapid and reliable way to identify the source tissue of a tumor metastasis.

77 Claims, 22 Drawing Sheets

OTHER PUBLICATIONS

Zhan et al, Neuroscience, 2002, 113/1:145-154.*
Paradis et al, Methods in Enzymology, 2002, 356:129-136.*
Jain, Methods in Enzymology, 2002, 356:157-167.*
Reilly et al, Brain Research Reviews, 2004, 46:225-233.*
Banks et al, Electrophoresis, 1999, 20/4-5:689-700.*
Emmert-Buck et al, Science, 1996, 274/5289:998-1001.*
Ornstein et al, Electrophoresis, 2000, 21:2235-2242.*
Banks et al., "The potential use of laser capture microidissection to selectively obtain distinct population of cells for proteomic analysis—Preliminary findings," *Electrophoresis* 20:689-700, Apr. 1999.
Cazares et al., "Discovery of prostate cancer biomarkers from laser capture microdissected (LCM) cells using innovative ProteinChipTM SELDI mass spectroscopy," *Proceedings of the American Association for Cancer Research Annual Meeting (91$^{st}$ Annual Meeting, San Francisco, CA, USA)* p. 851 (abstract), Mar. 2000.
Emmert-Buck et al., "An approach to proteomic analysis of human tumors," *Molecular Carcinogenesis* 27:158-165, Mar. 2000.
Emmert-Buck et al., "Protein fingerprinting of LCM-dissected human esophageal and prostate cancer by 2D-PAGE," *Proceedings of the American Association for Cancer Research Annual Meeting (90$^{th}$ Annual Meeting, Philadelphia, PA, USA)* 40(526):526 (abstract), Mar. 1999.
Simone et al., "Laser-capture micro-dissection: opening the microscopic frontier to molecular analysis," *Trends in Genetics* 14(7):272-276, Jul. 1, 1998.
Simone et al., "PSA quantitation in prostate cancer tissue cells procured by laser capture microdissection," *Proceedings of the American Association for Cancer Research Annual Meeting (90$^{th}$ Annual Meeting, Philadelphia, PA, USA)* 40:411 (abstract), Mar. 1999.
Emmert-Buck et al., *Am. J. Pathol.*, 145(6):1285-1290, 1994.
Klimek et al., *Carcingenesis*, 11(8):1377-1380, 1990.
Im et al., *J. Craniofacial Genetics & Dev. Biol.*, 3:281-288, 1983.
Moore et al., *J. Cell Biol.*, 105:1377-1386, 1987.
Pappalardo et al., *Seminars in Radiation Oncol.*, 8(3):217-223, 1998.

* cited by examiner

FIG. 3
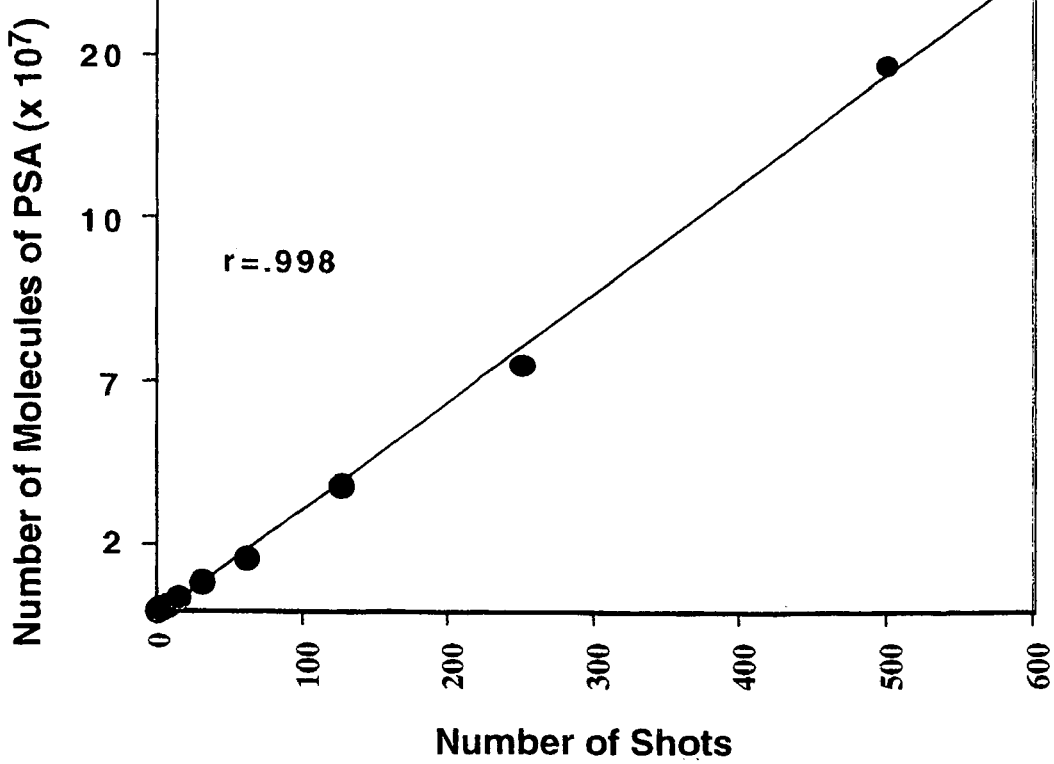
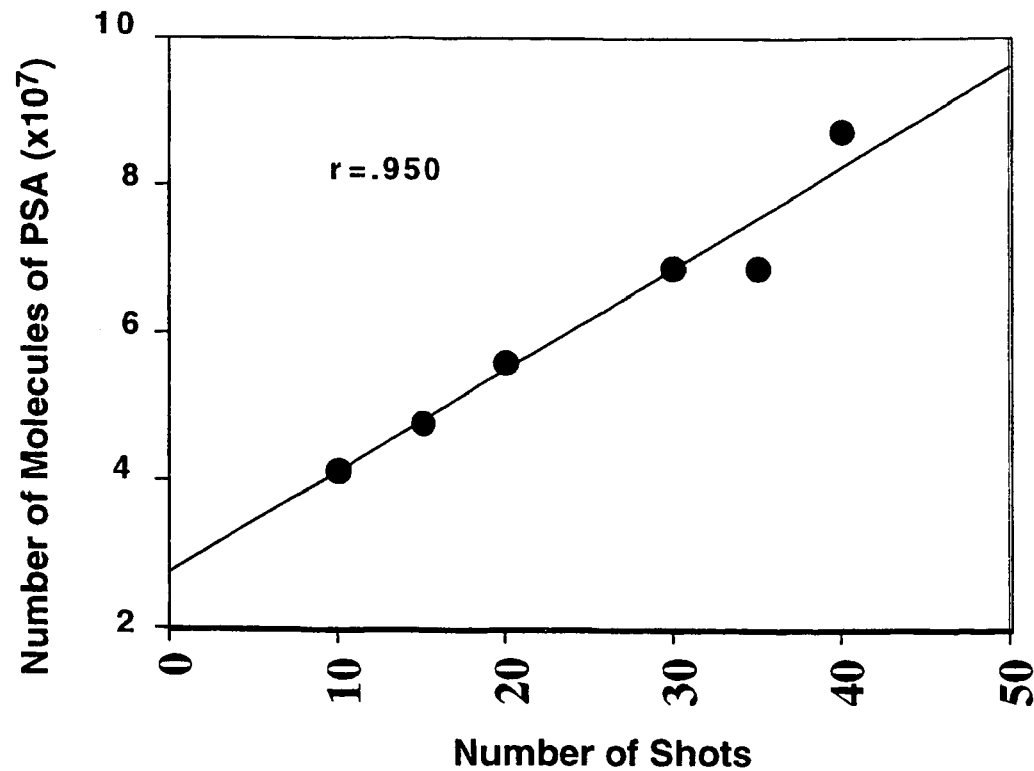

FIG. 4

| Sample | Mean PSA molecules (RLUs) | C.V.% | Mean no. cells |
|---|---|---|---|
| Prostate Tumor 100 shots (n=10) | $1.2 \times 10^8$ (7,199,673) | 3.9 % | 721 |
| Prostate Tumor 15 shots (n=10) | $1.9 \times 10^7$ (1,178,202) | 15.8 % | 78 |
| Prostate Tumor Single Shot (n=19) | $1.8 \times 10^6$ (708,730) | 54.7 % | 6.3 |
| Buffer Control (n=10) | Negative (88,788) | 3.5% | NA |
| Lung 100 shots (n=10) | Negative (134,413) | 6.5% | NA |
| Prostate Stroma 100 shots (n=6) | Negative (132,759) | 5.2% | NA |

FIG. 5

| Case Designation and Histologic Diagnosis | Molecules of PSA/Cell Mean per 100 shots | Immunohistochemistry Score |
|---|---|---|
| Case A Normal | $6.66 \times 10^4$ | + |
| Case B Tumor | $9.52 \times 10^4$ | + |
| Case C Tumor | $1.99 \times 10^4$ | + |
| Case B Normal | $1.04 \times 10^5$ | ++ |
| Case B PIN | $4.25 \times 10^5$ | ++ |
| Case C PIN | $3.70 \times 10^5$ | ++ |
| Case A Tumor | $3.4 \times 10^6$ | +++ |
| Case C Normal | $6.3 \times 10^6$ | +++ |

FIG. 12
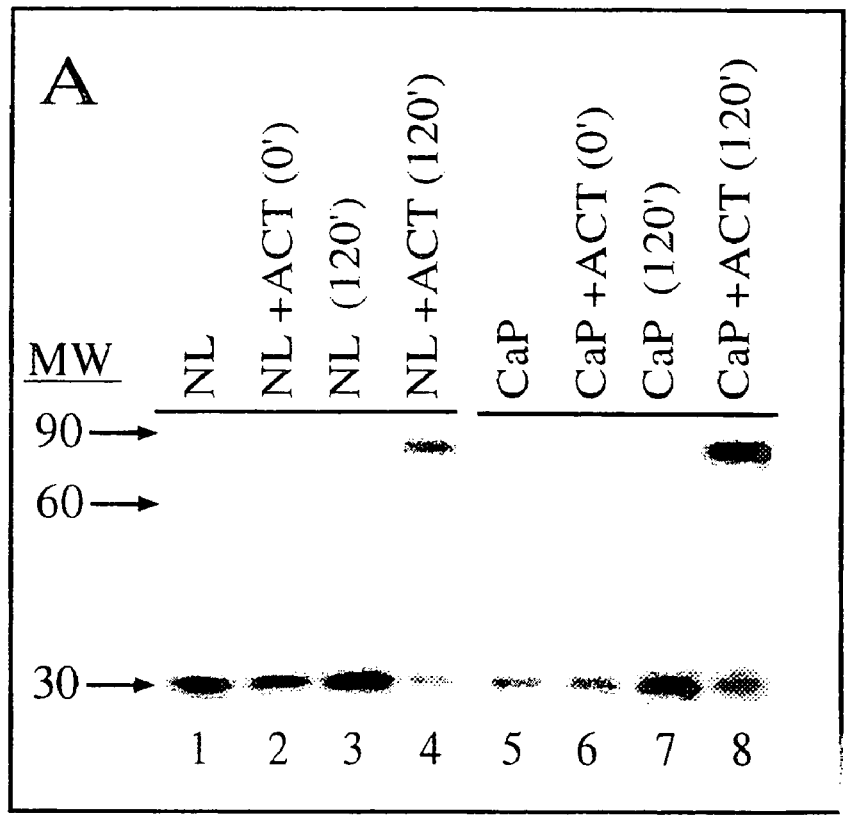
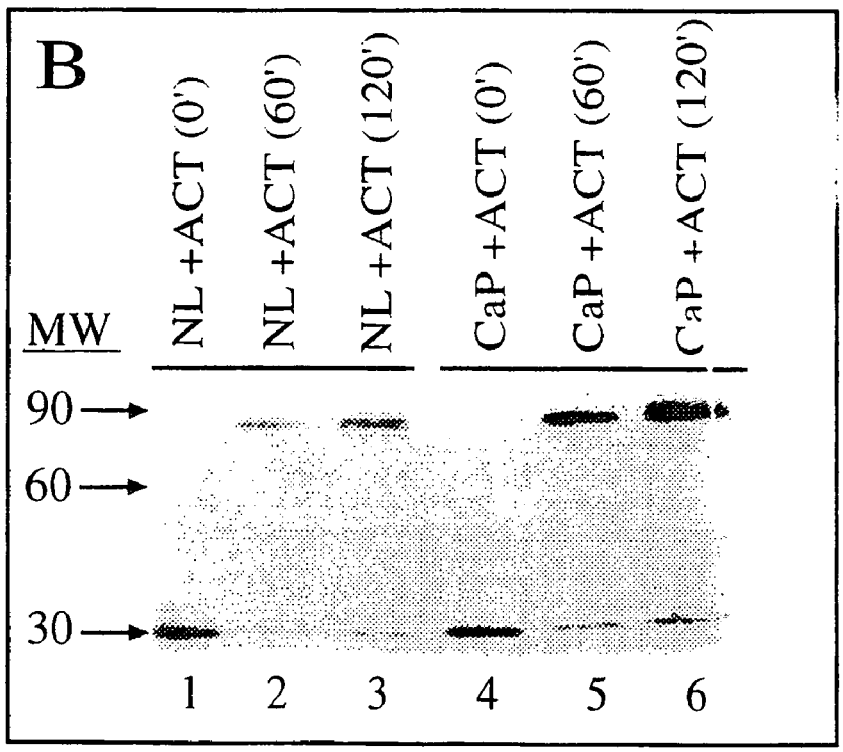

FIG. 15 Fingerprint comparison between a variety of tumor types

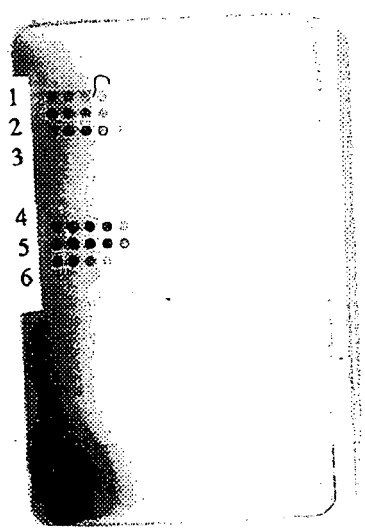
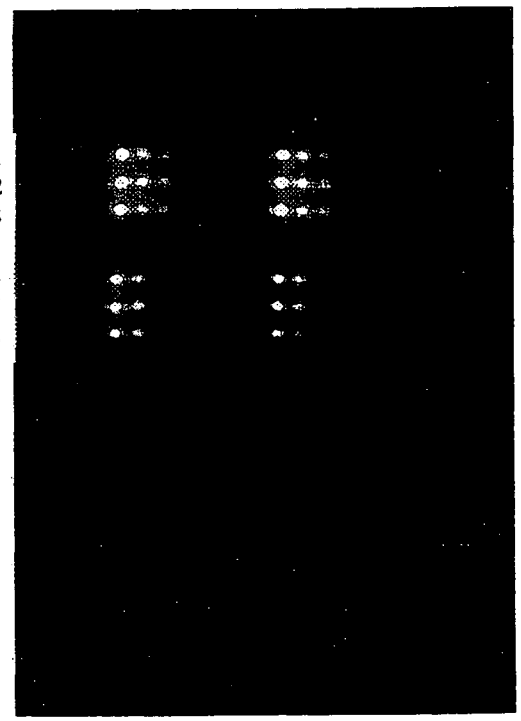
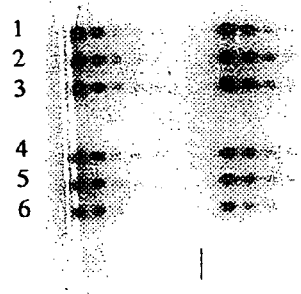
FIG. 20

FIG. 21
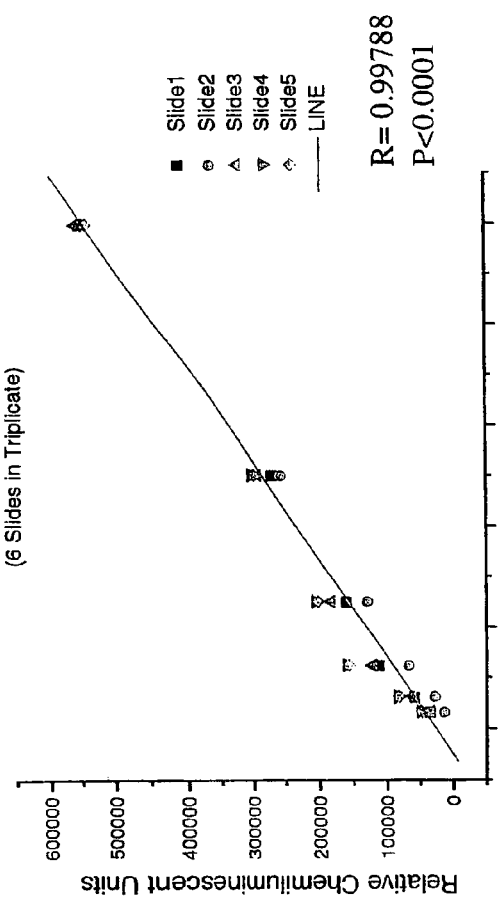
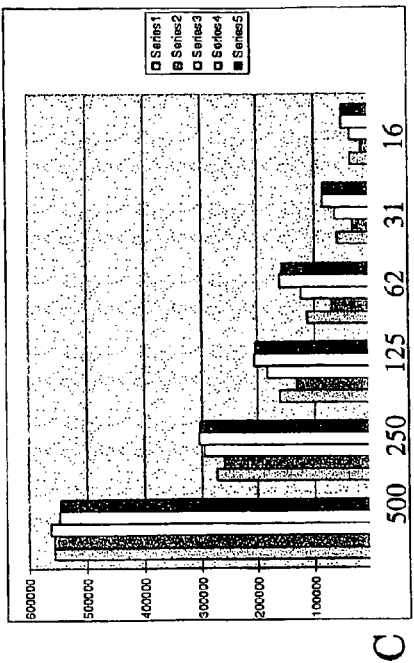
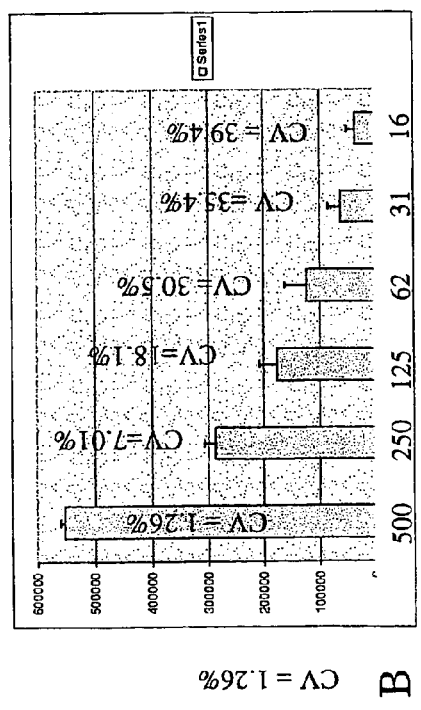

METHODS FOR THE ISOLATION AND ANALYSIS OF CELLULAR PROTEIN CONTENT

CROSS REFERENCE TO RELATED APPLICATIONS

This is the National Stage of International Application No. PCT/US00/04023, filed Feb. 16, 2000, and claims the benefit of U.S. Provisional Application No. 60/120,288, filed Feb. 16, 1999. The provisional application is incorporated herein in its entirety.

By this amendment the specification has been changed to reflect prior related applications. No new matter is added by this amendment.

BACKGROUND OF THE INVENTION

1. Field of the Invention

The present invention relates to methods and devices for the analysis of cell samples where the samples are pure populations or subpopulations of desired types. In particular, the present invention allows for direct comparison of protein content and protein characteristics between proteins isolated from tumor and normal cells from the same tissue sample.

2. Discussion of the Background

Proteomics is the study of variations in cellular protein levels between normal and disease states. As the field of molecular biology moves beyond genomics to proteomics, there is a growing need for a direct method to monitor the levels of expressed proteins in developing, diseased or genetically altered tissues. Direct monitoring of tissues is difficult because of their heterologous, three-dimensional structure. This structure is the result of the strong adhesive interaction of the various cell types with adjacent cells, connective stroma, blood vessels, glandular and muscle components, adipose cells, and inflammatory or immune cells. The amount and type of protein expressed by cells in such a native tissue environment may be quite different from that of more easily studied cultured or transplanted cells. This consideration requires a direct means of measuring protein levels to obtain results reflecting in vivo conditions.

Previous methods for extracting and analyzing protein macromolecules from tissue subpopulations have included UV laser ablation of unwanted tissue regions (Meirer-Ruge et al., *The laser in the Lowry technique for microdissection of freeze-dried tissue slices*, 8 Histochemical J. 384 (1976)) and oil well isolation of tissue cells (Matschinsky et al., *Quantitative histochemical analysis of glycolytic intermediates and cofactors with an oil well technique*, 16 (1) J. Histochemical Cytochem. 29 (1968)). These methods were complicated, labor intensive, and did not utilize protein stabilizers.

Because of these limitations, a number of direct comparisons between tumor cells and normal cells have not been achievable. There has been no way to directly compare, without the danger of cross-contamination, the spectrum of proteins contained in normal cells with the proteins in tumor cells in a single tissue. Many hypotheses about altered protein levels in tumor cells have been based on work on cells lines, and the ability for continued growth in culture by the cell line injects yet another variable into the results. There has also been no way to directly quantify differences in protein amount between tumor and normal tissue. Much of the work in this area has been done using immunohistochemistry, imparting the limitations as to quantification and specificity discussed above. Moreover, there has been no way to compare the protein content of various stages of tumor development, or to compare the characteristics of proteins found in tumor cells to those in normal cells. Nor could a protein's amino acid sequence or binding characteristics be performed. And, because such comparative protein studies could not be done, it was difficult to reliably determine the source of a tumor metastasis, unless the probable tumor source was already known.

SUMMARY OF THE DISCLOSURE

Proteomic research has been complicated by the fact that cells undergoing the progression to a diseased state may constitute less than 5% of the volume of a tissue biopsy sample. In a mixture of diseased and normal cells, differential protein expression in the diseased cells may be masked by the "background" of proteins expressed in normal cells. Immunohistochemistry cannot provide a solution to this problem, because it can provide only the location of the targeted antigen. This technique is ineffective at providing quantitative data because it is not possible to calibrate the intensity of immunohistochemical staining with the actual number of antigen molecules in the stained tissue cells. Additionally, many antibodies cannot differentiate between pro-enzyme and active enzyme species. Immunologically based studies cannot easily provide a complete picture of a cell's protein contents.

The present invention describes devices and methods for extracting proteins from samples of microdissected cells, and applying various analytic processes to the extracted proteins, such as immunoassays, 1D and 2D gel electrophoresis characterization, Western blotting, Matrix Assisted Laser Desorption Ionization/Time of Flight (MALDI/TOF), liquid chromatography quadrapole ion trap electrospray (LCQ-MS), and Surface Enhanced Laser Desorption Ionization Spectroscopy (SELDI). These methods allow for direct comparison of qualitative and quantitative protein content of tumor cells and normal cells from the same tissue sample. The methods also allow for investigation of protein characteristics of tumor cells, such as binding ability and amino acid sequence. The present methods also provide, through the use of protein fingerprinting, a rapid and reliable way to identify the source tissue of a tumor metastasis.

In this method, the protein content of a selected population of cells from a tissue sample is analyzed, by extracting the population of cells from the tissue sample using laser capture microdissection (LCM). The population of cells that is extracted can be, for example, cells of a particular cellular substructure (such as cells from epithelium on the lumen of an organ, or pockets of cells that have undergone malignant transformation against a background of a larger population of more normal cells). Proteins are isolated from the isolated population of cells, and characteristics of the proteins may be analyzed to provide information about the protein characteristics of the selected isolated population of cells.

In particularly disclosed examples, differential expression of proteins in isolated malignant cells can be used to study changing patterns of protein expression during malignant transformation. In other examples, cells at different stages of biological transformation (such as neoplastic progression from normal cells to metaplastic cells to invasive carcinoma) can be studied to analyze differential protein expression at different stages of neoplastic progression. Similar methods can be used to analyze cells for therapeutic purposes (such as selecting drugs targeted against expression of particular proteins), or in drug response assays (to assess changes in protein expression as an indication of drug response).

BRIEF DESCRIPTION OF THE DRAWINGS

FIGS. 3A and B are graphic representations of the number of molecules of PSA as compared to the number of laser shots used to harvest the cells. FIG. 3A shows the results of a 500 shot sample of tumor cells serially diluted to verify sensitivity. RLU values were converted to PSA molecule numbers. Linear regression indicated an r value of 0.998. FIG. 3B reports the results of a linearity analysis conducted on six different tissue sections from the same patients. The number of laser shots are indicated, r=0.95.

FIG. 4 is a table showing the number of PSA molecules, the coefficient of variation of the process, and the mean number of cells used in the immunoassays. These sensitivity and precision analyses were done on 10 separated microdissection replicates. The mean readout in RLUs is reported as well as the corresponding number of PSA molecules. The sensitivity, defined as two standard deviations above background, was one laser shot. Imprecision (% CV) was inversely correlated with number of shots per specimen.

FIG. 5 is a table comparing the number of PSA molecules with the immunohistochemistry score. Independent immunohistochemistry scoring of coded specimens was done by a pathologist and scored as high (+++), medium (++), and low (+). PIN: prostate intraepithelial neoplasia, Tumor: invasive carcinoma, Normal: histologically normal prostate glands. The relative concentrations of PSA per cell among different progression stages varies greatly and this corresponds directly to the semiquantitative immunohistochemistry scoring.

FIGS. 6A, B, and C are 2-D or 1-D gel comparisons of the proteins in microdissected normal and tumor epithelium. Fifty thousand cells were procured by LCM, directly lysed in IEF buffer and run on a 3–10 NL Pharmacia IPG IEF strip for 100 kVhr. The second dimension runs were performed on 8–18% linear gradient SDS-PAGE gels and the gels were stained with silver. FIGS. 6A and 6B show match tumor and normal fingerprints for each patient. A representative pI and molecular weight ruler for direct comparison and alignment is shown in panel A. FIG. 6C shows the alpha-tubulin immunoblot that was used to normalize for relative protein load.

FIGS. 12A and B are anti-PSA Western blots showing complexed and non-complexed species.

FIG. 13A shows two separate microdissections of prostate tumor epithelium from the same tissue section from the same patient (1200 cells each) which were analyzed by SELDI protein fingerprinting. The raw mass spectroscopic mass map is shown for each microdissection along with the Gel-View® display from the same data set.

FIGS. 14A, B, and C show that SELDI protein profiles of LCM-derived cellular lysates are discriminatory between different tumor epithelial cell types from different patients and between tumor and normal epithelial cells from the same patient. In FIGS. 14A and 14B LCM derived tumor epithelial cells (1200 cells) from prostate, breast, and colon frozen tissue sections were separately acquired and analyzed via SELDI. The Gel-View® representation is shown in FIG. 14A and the spectrographic mass profile is shown in panel B. FIG. 14C shows the SELDI analysis of four separate patient-matched microdissections of 1200 cells of colon normal epithelium, colon tumor epithelium, colon tumor epithelium from the colon tumor that has metastasized to the liver, and normal liver cells next to the metastasis. The Gel-View® display is shown as a representation of the direct alignment of each of these four mass spectra to each other.

FIGS. 18A and 18B are SELDI analyses of 8 different esophageal cancer cases, where three separate microdissections of eight different patients' matched tumor and normal cells were subjected to SELDI analysis via the use of a hydrophobic interaction C18 binding surface. Each replicate was run in triplicate, giving a total of 72 data points for each protein peak analyzed. The analysis of the protein fingerprint in the low mass region is shown in FIG. 17A, the higher mass region in FIG. 17B. A representative mass map from one case (case #1) is shown on the left side of each panel with the normal and tumor fingerprint shown (top and bottom, respectively) for each mass region. A gel-like representation is displayed for that particular case as well as the fingerprint for two other cases.

Proteins 1, 2, 6, and 7 are labeled for orientation. All cases analyzed in the study set were then subjected to analysis as a ration of relative intensity of the selected proteins to one another and the statistical results shown on the right side of each figure. FIG. 17A: average C.V.=12.7%, 29.4% for the normal and tumor microdissections respectively. FIG. 17B: average C.V.=10.5% and 18.9% for the normal and tumor microdissections, respectively.

FIG. 18A shows a mass map that represents the profile from 1500 normal, pre-invasive neoplasia (PIN) and invasive carcinoma cells acquired by LCM from one case (case #2). Additionally, the corresponding patient-matched stromal cells (1500 cells) were also microdissected for analysis. FIG. 18B shows a gel-like image of the raw mass data shown in Panel A. All samples from this patient were run in triplicate, with the representation of one experiment shown. Two proteins, A and B, having molecular weights of 28,000 and 32,000 respectively, were found to be reproducibly differentially expressed in this patient and are indicated in both FIGS. 18A and 18B. FIG. 18C shows the ratio analysis of A vs. B from an additional study set of two other (cases #1 and #3) patient matched tumor and normal prostatic epithelium (average C.V>=17.2% and 10.1% for the tumor and normal microdissections, respectively).

FIGS. 20A, 20B and 20C are representative results using colorimetric and chemiluminescent detection methods for prostate soluble antigen (PSA). The rows of the upper arrays are in all three cases (1) a protein standard, (2) prostate stroma, and (3) normal prostate tissue, while the lower arrays include (4) prostate intraepithelial neoplasia (PIN), (5) tumor tissue, and (6) invasive tumor tissue. The amount of total protein loaded on the gel is reduced across the rows. FIG. 20A shows the colorimetric results, FIG. 20B is the positive and FIG. 20C is the negative image of the fluorescence results.

FIGS. 21A, 21B, and 21C diagram the reproducibility of protein analysis for samples microdissected from a mixed sample of epithelial cells of the esophagus. All the following data was obtained from normal cells present in the sample. FIG. 21A shows the reproducibility of the annexin I protein data in normal cells over a variation of "shot" size within one slide and between multiple slide sets. FIG. 21B shows a histogram of the coefficient of variance for these data sets. FIG. 21C graphically shows reproducibility of the total protein obtained from the cells as shown by fluorescence detection.

DETAILED DESCRIPTION OF THE INVENTION

Figure 1:
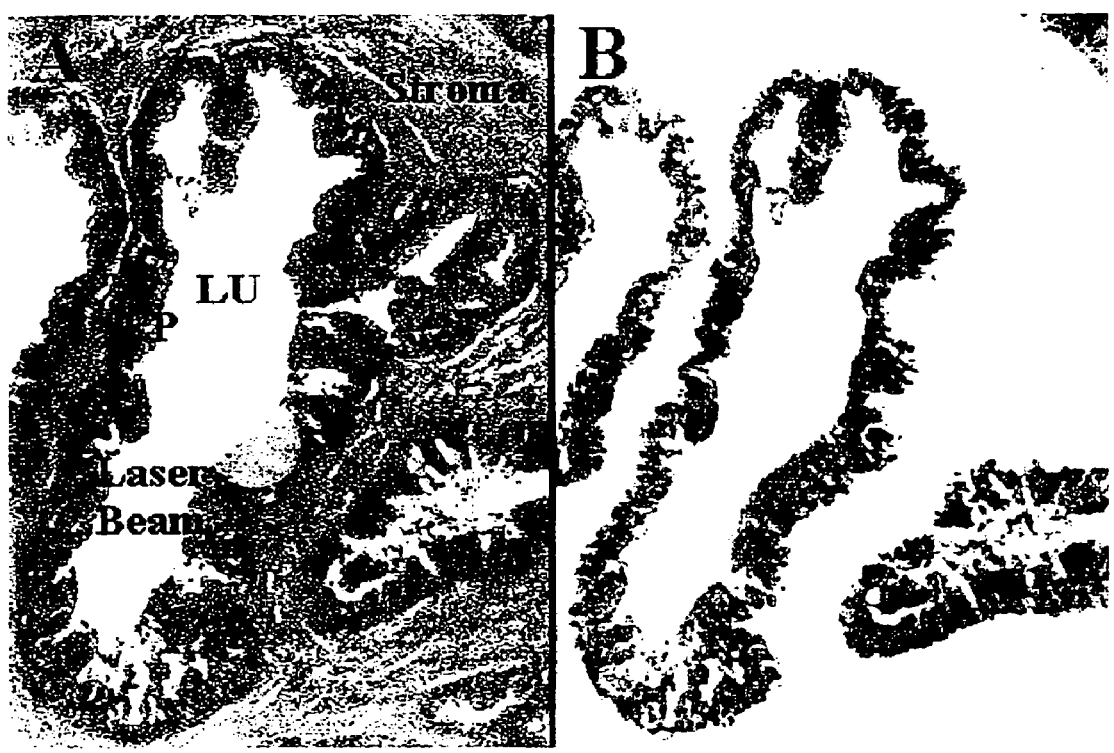
FIG. 1 is a relative size comparison of the laser beam diameter and the epithelial tissue sample being microdissected. Laser Capture Microdissection (LCM) was performed to selectively transfer only the epithelial lining of the prostate gland to the polymer film. The 30 micron laser beam spot size is shown in relation to the thickness of the gland. EP: epithelial, LU: lumen, stroma are as marked.

Laser Capture Microdissection (LCM) is a recently developed technology that enables the user to obtain pure cell populations from stained heterogeneous tissue under direct, high power microscopic visualization. See Emmert-Buck et al., *Laser Capture Microdissection,* 274 Science 998 (1996); Bonner et al., *Laser Capture Microdissection: Molecular Analysis of Tissue,* 278 Science 1481 (1997). A laser beam focally activates a special transfer film that specifically bonds to cells identified and targeted by microscopy within the tissue section. The transfer film with the bonded cells is then lifted off the thin tissue section, leaving all unwanted cells behind. This process allows the sample to include only cells exhibiting the desired morphology for study. This application of LCM to the analysis of the DNA of isolated cells is described in U.S. Pat. No. 5,843,657, issued to Liotta et al., which is incorporated by reference.

Briefly, the LCM process works as follows. First, the transparent transfer film is applied to the surface of the tissue section. Under the microscope, the operator views the thin tissue section through the glass slide on which it is mounted and chooses microscopic clusters of cells to study. When the cells of choice are in the center of the field of view, the operator pushes a button that activates a near IF laser diode integrated with the microscope optics. The pulsed laser beam activates a precise spot on the transfer film immediately above the cells of interest. At this precise location the film melts and fuses with the underlying cells of choice. When the film is removed, the chosen cell(s) are tightly held within the focally expanded polymer, while the rest of the tissue is left behind. The exact morphology of the procured cells is retained and held on the transfer film, ensuring preservation of the cells' intracellular components such as DNA, RNA, and proteins for future analysis. The removed transfer film and cells are transferred onto a plastic cap (referred to as the LCM cap) for subsequent analysis.

Isolation of these preserved intracellular components from the cells on the LCM cap has necessitated the development of new procedures, buffers, and devices. In particular, the present methods utilize a new procedure for extracting proteins from very small sample sizes, on the order of about 1500 to about 5 cells, the number obtained in a typical LCM laser shot. This procedure generally involves the extraction of proteins in one solubilizing step, using a very small volume of a unique buffer. To facilitate the handling of such small volumes and small sample sizes, a device in which the solubilization step can be conveniently performed was developed. The results of this new procedure are intact proteins, substantially free of cross-contamination from other nontumor or normal cell types. The isolated proteins maintain activity, allowing analysis through any number of immunological and biochemical assays.

The buffers for the protein isolation step can include one or more of buffer components, salt, detergents, protease inhibitors, and phosphatase inhibitors. In particular, one effective buffer for extracting proteins to be analyzed by immunohistochemistry includes the buffer Tris-HCl, NaCl, the detergents Nonidet® P-40, EDTA, and sodium pyrophosphate, the protease inhibitors aprotinin and leupeptin, and the phosphatase inhibitors sodium deoxycholate, sodium orthovanadate, and 4-2-aminoethyl benzenesulfonylfluroride (AEBSF). Another salt which could be used is LiCl, while glycerol is a suitable emulsifying agent that can be added to the fraction buffer. Additional protease inhibitors include soybean trypsin inhibitor and pepstatin. Other suitable phosphatase inhibitors include phenylmethylsufonyl fluoride, sodium molybdate, sodium fluoride, and beta-glycerol phosphate. For 2-D gel analysis, simple lysis with a 1% SDS solution was effective, while ultimate analysis using the SELDI process required Triton-X-100, a detergent (Sigma, St. Louis, Mo.), MEGA 10® (ICN, Aurora, Ohio), and octyl B-glucopyranoside (ESA, Chelmsford, Mass.) in a standard PBS base. Another buffer which was used prior to 2-D gel analysis was 7M urea, 2M thiourea, CHAPS, MEGA 10, octyl B-glucopyranoside, Tris, DTT, tributyl phosphine, and Pharmalytes. A preferred 1:100 concentration buffer is as follows:

| Material | Concentration of Stock Solution | Amount |
| --- | --- | --- |
| 50 mM Tris-HCL | 1 M | 1.25 ml |
| 1% NP-40 | 10% | 2.5 ml |
| .1% Na Deoxycholate | 10% | 250 µl |
| 150 mM NaCl | 3 M | 1.25 ml |
| 4 mM EDTA | .25 M | 400 µl |
| Aprotinin | 10 mg/ml | 25 µl |
| Leupeptin | 10 mg/ml | 25 µl |
| 10 mM Na Pyrophosphate | | .115 g |
| 2 mM Na Orthovanadate | | .004 g |
| AEBSF | 100 mM | 250 µl |

The buffer is made and diluted 1:100 in distilled water for use. The buffer must be kept frozen at −20° C. It can only be used unfrozen for a few hours. In all cases, the buffer is used in very low volumes, from about 1 µl to about 15 µl, and is applied directly to the laser capture dissected cells while still on the LCM cap.

Figure 16:
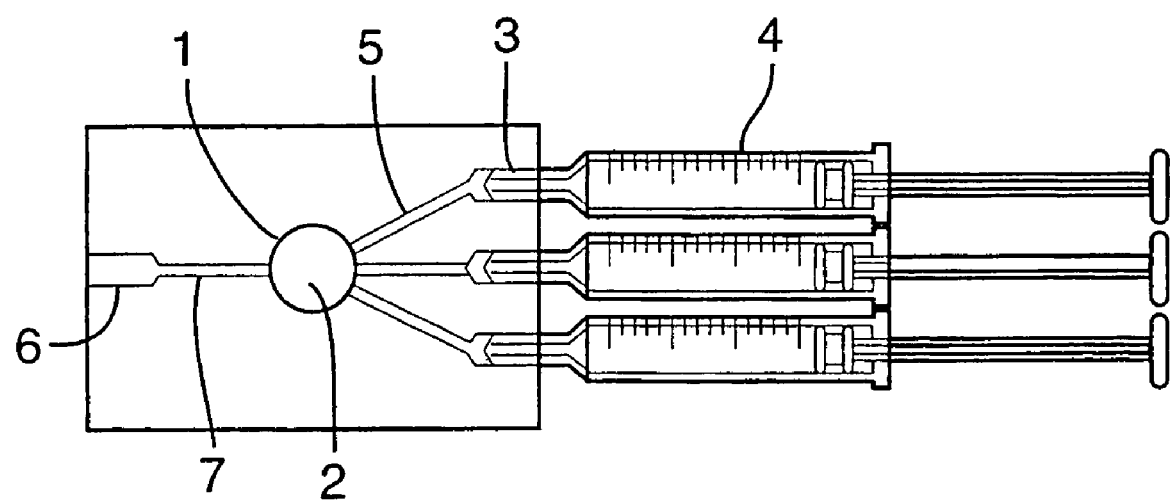
FIG. 16 shows a device developed for solubilizing proteins in cells taken from a biological specimen by LCM.

To simplify the process of solubilizing the proteins directly on the LCM cap, a device was developed to handle the small volumes. This device (shown in FIG. 16) includes a small chamber 1 where the solubilization process can occur. The chamber has an upper opening 2 structured such that it can directly accept the LCM cap with its adhered cells. The LCM cap is placed in the chamber 1 with the surface having cells upon it facing the interior of the chamber. Once the LCM cap is attached to the device, the cells are therefore strategically positioned within the chamber and solubilization of the proteins will occur upon introduction of the solubilization buffer. The chamber is supplied with at least one inlet port 3, which can be equipped with a syringe 4 as a means of introducing the small volume of the solubilizing buffer into the chamber 1. The inlet port 3 is connected to the chamber by a narrow inlet canal 5, where liquids placed into the canal will move toward the solubilization chamber by capillary action. The device can include more than one inlet chamber, if desired, each equipped with a means of introducing liquid, such as a syringe. The device also includes an outlet port 6, connected to the chamber 1 with a narrow outlet canal 7, which can be supplied with a means of collecting and removing the solubilized proteins. One embodiment of this device has the chamber 1, the inlet ports 3, inlet canals 5, outlet port 6, and outlet canal 7, all machined in a hard plastic block, such as lucite.

Once the proteins have been solubilized, a number of different immunological or biochemical analyses can be used to characterize the isolated proteins. Because the cells are usually initially identified for LCM capture based on particular morphological characteristics, the results of these assays are assured to be representative of the cell type collected.

One type of assay that can be performed is a soluble immunoassay, where an antibody specific for a protein of interest is used. The antibody can be labeled with a variety of markers, such as chemiluminescence, fluorescence and radioactive markers. For best results, the assay used should be of high sensitivity, such as a microparticle enzyme immunoassay (MEIA). By applying a calibration curve used to estimate immunodetected molecules in serum, the number of molecules per cell can be estimated. Thus, the presently described methods provide a quantitative immunoassay, which can measure the actual number of the protein molecules of interest in vivo.

A second type of assay that can be used to analyze the extracted proteins is two-dimensional polyacrylamide gel electrophoresis (2D PAGE). By running both proteins extracted from normal cells of the sample and proteins extracted from tumors cells of a sample, and comparing the blots, differential protein expression can be seen. In particular, by scanning the stained gels into a computer, and using image comparison software, the location of proteins that are present in one cell type and absent in the other can be determined. Furthermore, these altered proteins can be isolated from the gel where they are present, and mass spectroscopy MS-MS sequencing can be used to identify the protein, if the sequence exists in a database. In this way, the protein differences between normal and tumor cells can be more fully understood. Additionally, proteins of interest isolated from a 2-D gel may be used in binding studies, where the protein is functionally tested for an alteration in the ability to bind with a putative or known ligand. Finally, this comparative analysis need not be between normal and tumor cells, but can be between isolated stages of a tumor, where the different stages exhibit sufficient morphological differences to allow separate isolation of populations using the LCM technique.

A further analysis that may be performed involves the use of the surface enhanced laser desorption ionization spectroscopy technique, or SELDI (Ciphergen Biosystems Inc., Palo Alto, Calif.). This process can separate proteins which would not be separately focused by 2-D gel analysis, in particular those proteins which are very basic, very small (<7000 daltons) or are expressed at low or moderate levels in the cells. The lower level of expression becomes critical in these experiments because of the extremely small sample size of cells used. SELDI also separates proteins more rapidly than gel analysis. SELDI utilizes a "protein chip" that allows for desorption and detection of intact proteins at the femtomole levels from crude samples. Proteins of interest are directly applied to a defined small surface area of the protein chip formatted in 8 to 24 predetermined regions on an aluminum support. These surfaces are coated with defined chemical "bait" matrices comprised of standard chromatographic supports, such as hydrophobic, cationic, or anionic or biochemical bait molecules such as purified protein ligands, receptors, antibodies, or DNA oligonucleotides. See Strauss, New ways to probe the molecules of life, 282 Science 1406 (1998). In the case of LCM collected samples, the solubilized proteins are applied to the surface of the SELDI chip. Binding of the proteins to the surface is dependent on the nature of the bait surface and the wash conditions employed. The mixture of bound proteins is then characterized by laser desorption and ionization and subsequent time of flight mass analysis generated from a sensitive molecular weight detector. This data produces a protein fingerprint for the sample, with SELDI having a practical resolution and detection working range of 1000 to 300,000 daltons, depending on the energy absorbing molecule utilized and the bait surface/wash conditions employed.

The produced protein fingerprints have proven to be both disease-specific and organ-specific. That is to say, the protein fingerprint of a tumor from a particular tissue type remains characteristic of that tissue type, whether it is normal, tumor, or a metastasis. This allows a determination of the origin of an unknown metastasis to be made, through comparison to protein fingerprints of normal or tumor tissue of likely organ sources.

The principles of the invention are further illustrated by the following Examples.

EXAMPLE 1

Quantification of Intracellular PSA from Benign and Malignant Prostate Epithelium by Immunoassay Case Materials Tissue was obtained following an IRB approved protocol from both the Urologic Oncology Branch in the National Cancer Institute, Bethesda, Md. and the Mayo Clinic in Rochester Minn. After surgery, the tissue samples were snap frozen in liquid nitrogen. The tissue was then embedded in Optical Coherence Tomography (O.C.T.) compound (Tissue Tek, Miles, Elkhart, Ind.) and stored at −80° C. Cases were selected based on the histology present in the tissue sections so that normal glands, Prostate Intraepithelial Neoplasia (PIN), and adjacent carcinoma, could be compared within the same patient. Prostate tissue cases were selected to include ample stroma to serve as a negative control. Lung tissue was used as a second negative control.

Sectioning and Staining

The O.C.T embedded tissue blocks were cut into 8 μm sections with a cryostat. After cutting, the sections were immediately placed on dry ice and then stored at −80° C. Only one section was thawed and dissected at a time, to minimize degradation of proteins. After fixation in 70% ethanol for 10 s, the section was stained with hematoxylin and eosin, and dehydrated in xylene.

Laser Capture Microdissection

The PixCell system incorporates an Olympus IX-50 Microscope containing a microscope slide stage which is moved by a joystick. The operator uses the joystick to position the tissue under a fixed laser beam that can be focused from 5 to 60 μm in diameter. The LCM transfer film is fixed to the undersurface of a vial cap (CapSure® TF-100 transfer film carrier, 5 mm dia. optical grade transparent plastic; matching vial is Brinkmann #22 36 430-8). LCM cell procurement time was always less than 15 minutes. A droplet of the extraction buffer was applied to the surface of the film containing the selected cells. The cap with the droplet on its undersurface was inserted into the mouth of the matching vial containing 50 μl of the immunoassay dilution buffer. The sealed vial sample receptacle was frozen at −20° C. and stored for less than 48 hours prior to assay. The thawed sample was held at 4° C. for no longer than 2.5 hours prior to introduction into the immunoassay module.

FIG. 1 compares the size of a 30 μm laser shot with the size of an example prostate gland that was microdissected by movement of the joystick. The yield of procured pure epithelial or carcinoma cells, and the precision of cellular procurement, were tested by visually counting the number of cells removed from the tissue and transferred to the film. Table 1 compares the number of laser shots with the average total number of microtissected cells.

TABLE 1

|  | 1 shot case C | 15 shots case C | 100 shots case B |
|---|---|---|---|
| Mean Cells | 6.78 | 102 | 506.2 |
| Standard Deviation | 3.73 | 3.39 | 11.98 |
| Coefficient of Variation | 55.1% | 3.33% | 2.37% |

A standard laser spot diameter of 30 μm encompasses 5–7 cells. Individual tissue cells can vary in their packing density, their shape and their volume. Consequently, the imprecision of the cell yield is greater with fewer laser shots.

Solubilization of Proteins from LCM Procured Cells

Figure 2:
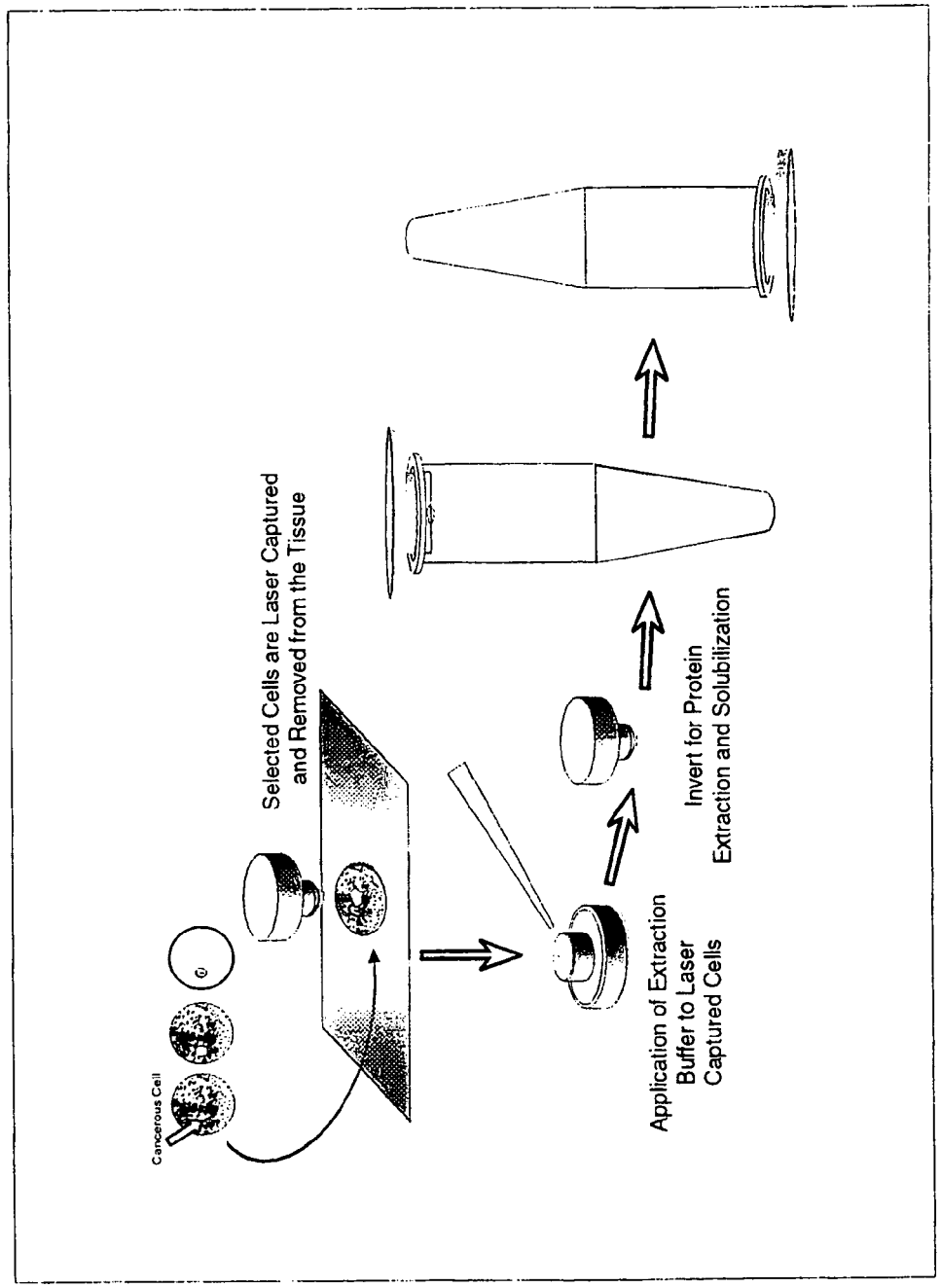
FIG. 2 shows how cells of interest are selected using LCM and transferred onto a cap, where the proteins are solubilized directly into a tube.

Extraction of the proteins from the exposed transferred cells was done by pipetting a small volume of buffer directly on the inverted capture surface of the polymer film (FIG. 2). Following placement of 5 μl of extraction buffer onto the transfer surface containing the tissue cells, visual confirmation was obtained establishing the complete solubilization of the stained cells. The transfer cap with the extracted cellular protein was inserted into the mouth of a vial containing the immunoassay buffer. After analysis, the transfer caps were counterstained to ensure complete solubilization of the cells. The diluted extraction buffer did not interfere with the immunoassay background level or linear calibration.

Extraction Buffer

The final buffer composition was a 1/1000 dilution of the following stock: 50 mM Tris HCl, 1% NP-40, 0.1% Na Deoxycholate, 150 mM NaCl, 4 mM EDTA, Aprotinin (10 mg/ml), Leupeptin (10 mg/ml), Na Pyrophosphate (10 mM) Na orthovanate (2 mM), and AEBSF (100 mM).

Assay Principle

The Immulite Third Generation PSA assay (Diagnostic Products Corp., Los Angeles, Calif.) was adapted to measure PSA solubilized from tissue cells procured by LCM. Photon production is measured by a luminometer (output: relative light units (RLUs)). Negative tissues or zero controls produced a value of 80140,000 RLUs, compared to PSA positive samples that ranged from 600,000 to 10,000,000 RLUs.

PSA Immunoassay: Microparticle Enzyme Immunoassay (MEIA)

PSA was measured by an automated two site chemiluminescent assay, using the ultrasensitive PSA reagent kit on the Immulite immunoassay analyzer (Diagnostic Products Corp., Los Angeles, Calif.). RLUs reflect the photons detected by the photomultiplier tube, which is proportional to the concentration of PSA. The sensitivity of the assay is 0.004 ng/mL of PSA, or approximately $4 \times 10^6$ molecules of PSA per assay.

Immunohistochemistry

Immunohistochemistry staining for PSA was conducted as follows. The frozen sections were desiccated and then fixed in acetone. Following a wash with 3% goat serum, primary antibody incubation was 1 hour at room temperature. The secondary antibody was labeled by Avidin/Biotin and the substrate system was Peroxidase/DAB. The secondary reaction was performed essentially as suggested by the commercial product insert.

Calibration Curve

The calibration curve used for measurement of PSA in serum according to the Immulite package insert was applied to the measurement of cellular tissue proteins procured by LCM. The calibration curve designed for serum was reproduced with the LCM extracted cellular proteins in the buffer solution. Serum or buffer samples with a known concentration of PSA were mixed with equal volumes of 100 laser shots of PSA negative tissue cells. There was approximately 100% recovery in all cases, with no detectable elevation of the zero dose or diminution of the signal. The number of laser shots of actual tissue cells was compared to the calculated number of PSA molecules for individual patient cases as shown in FIG. 3. Linear regression analysis yielded an r value of greater than 0.95 over a dynamic range of 0.004 ng/mL to 1 ng/mL.

Sensitivity

The detection limit of the assay for microdissected cellular proteins was 0.004 ng/ml PSA as defined as the concentration two standard deviations above the signal response of a sample free of PSA or a PSA negative tissue. The sensitivity achieved with these criteria was one 30 μm laser shot (5–7 cells).

Imprecision

The imprecision of cell capture for 100 shots is 3.3% C.V. compared to a C.V. of 15.8% for the PSA measured in the proteins extracted from 15 laser shots. In keeping with the assumed biologic heterogeneity, one laser shot exhibits a PSA measurement C.V. of 60.2%, even though the mean magnitude of the signal (804,416 RLUs) is substantially greater than the mean value for combined 100 shots of background tissue (132,759) (FIG. 4). Thus, capturing 15 (analytical sensitivity threshold) to 100 laser shots of a tissue sample (this takes less than five minutes) provides an acceptable level of imprecision for a routine assay.

Correlation with Tissue Immunohistochemistry

Analysis using LCM coupled with PSA immunoassays for PSA was conducted on prostate tissue sections that contained normal epithelium, carcinoma, and prostate intraepithelial neoplasia (PIN). Based on the imprecision analysis described above, the number of laser shots was 100. For each specimen studied, a standard curve was prepared for a series of different numbers of laser shots to verify that conclusions based on 100 shots remained in the linear portion of the curve (FIG. 3B). Immunohistochemistry for Prostate Specific Antigen was conducted on adjacent sections. The PSA immunoreactivity of cellular populations identical to those sampled by LCM on matched coded sections was scored independently and ranked on a scale of zero to five plus (FIG. 5). The average number of molecules per cell ranged from $10^4$ to $10^6$. The immunohistochemistry scoring values paralleled the quantitation and mirrored the heterogeneity in PSA production by normal and neoplastic cell populations. For example, in case C the normal epithelium contained $6.3 \times 10^6$ molecules and scored three plus by immunohistochemistry. In contrast, the PIN cells contained $3.7 \times 10^5$ molecules and scored two plus, and the tumor cells contained $1.99 \times 10^4$, and stained one plus.

Application of this new technology, as reported in FIG. 5, provides quantitative confirmation of the heterogeneity in PSA expression that was previously detected only by qualitative staining. The average numbers of PSA molecules harvested per cell ranged over several logs. An immunohistochemical staining difference could be discriminated only if there was greater than a ten-fold difference in PSA molecule number per cell.

The present technology provides one of the first direct estimates of the actual number of protein molecules per tissue cell in vivo for a single specific known protein of moderate to low abundance. The number of total PSA molecules in normal prostate epithelium ranged from $10^4$ to $10^6$. PSA is an important serum analyte used to clinically monitor prostate cancer, but it is not a specific maker of prostate cancer. Previous investigators have reported great heterogeneity in the intensity of PSA immunohistochemical staining among various neoplastic and non-neoplastic populations in the prostate. Populations of microdissected cells of a pure histologic class would be expected to contain some level of heterogeneity in PSA expression among the population members, as presently seen.

EXAMPLE 2

Comparative Protein Analysis of Normal and Cancerous Esophageal Epithelium Patients and Tissue Samples The two specimens studied were from patients who presented to the Shanxi cancer Hospital in Taiyuan, Shanxi Province, People's Republic of China and diagnosed with esophageal cancer. Both patients were considered candidates for curative surgical resection. Both cases were stage two squamous cell carcinomas of the esophagus.

Microdissection

Frozen section slides were prepared from each case and microdissected by LCM (Pixcell 100, Arcturus Engineering, Mountain View, Calif.) by selectively aiming for and capturing normal epithelium or tumor cells. LCM was performed as previously described except AEBSF (Boeringer Manheim) was added to the staining baths at a final concentration of 2 mM to inhibit proteases. In each case 50,000 cells were procured. Based on careful review of the histologic sections each microdissection is estimated to contain >98% of desired cells (normal versus tumor).

Sample Preparation

One hundred microliters of IEF lysing solution containing 7M Urea, 2M Thiourea, 4% CHAPS, 1% MEGA-10, 1% Octyl-b-Glucopyranoside, 40 mM Tris, 50 mM DTT, and 2 mM tri-butyl phosphine (TBP) and 0.5% (v/v) Pharmalytes was applied directly to the microdissected cells adhered on the LCM cap, placed into an eppendorf tube and vortexed vigorously for one minute until all cells were completely lysed. The IEF lysing solution was then re-applied to another cap containing cells from the same microdissected material and the procedure repeated until each 100 μl contained lysate from 50,000 cells (approximately 7000 LCM transfer pulses).

2D PAGE and Image Analysis

First-dimension isoelectric focusing was carried out on a Pharmacia Immobiline IPG Dry-strip system essentially as described by the manufacturer. Pre-cast immobilized pH gradient strips (18 cm, 3–10 non-linear) were employed for the first dimensional separation for a total focusing time of 120 kVh. The strips were re-equilibrated with a solution containing SDS and Tris pH 6.9, reduced with TBP (2 mM), alkylated with iodoactemide (2.5% w/v), and directly applied to a 8–18% linear gradient SDS-PAGE gel for electrophoresis overnight at 40 volts constant voltage. The gels were stained with silver and direct scanning and image analysis was performed using an Umax scanner with Adobe Photoshop software and a Tektronix IISDX photographic-quality printer. Scanned images were analyzed and compared using the MELANIE II software package (BioRad). Comparison of protein fingerprints were performed using images representing protein spots readily apparent by direct visualization. Only spots that were present/completely absent between normal-tumor cells were defined as altered. Each experiment was performed in duplicate and produced similar results (data not shown). Normalization of sample load was by anti-alpha-tubulin immunoblot analysis prior to the first-dimension run. Scoring of the blots included comparison of multiple exposure times.

Analysis of Alpha-Tubulin

Ten µl of the IEF lysate was diluted 1:1 in 2X SDS sample buffer, boiled for 5 minutes, and applied to a 4–20% NOVEX Tris-glycine SDS gel and electrophoresed for 1 hour. Immunoblotting was performed for 1.5 hour using a BIO-RAD Semidry blotting apparatus with Immobilon PVDF membrane as the capture surface. Blots were blocked with 1X TBS containing 1% ovalbumin and incubated with a monoclonal anti-alpha tubulin antibody for 3 hours. Anti-alpha tubulin antibodies were purchased from SIGMA and used at final dilution of 1:1000. Blots were washed with 1X TBS 3 times for 5 minutes and secondary antibody was added. HRP-coupled rabbit anti-mouse secondary antibodies were purchased from SIGMA and used at a final dilution of 1:10,000. Blots were washed and ECL substrate (Amersham) was added for chemiluminescent detection via autoradiography on Kodak Bio-Max film.

Mass Spectrometry

A separate 2D PAGE gel was run with microdissected tumor from case #1 except the gel was stained and analyzed with zinc-imidazole. Two proteins which were aberrantly regulated in both tumors were chosen for mass spectrometry MS-MS sequencing. The acrylamide plug was taken from the gel and washed once with HPLC-grade water for 5 minutes, and subjected to in gel tryptic digestion as previously described.

In-Gel Proteolytic Digestion

Gel pieces were excised and washed by end-over-end mixing in 12 ml 30% methanol for 30 minutes (room temperature), washed twice for 30 minutes with 150 µl of 1:1 acetonitrile/100 mM ammonium bicarbonate pH 8. Each spot was sliced into fourths and rehydrated 10 µl of 100 mM ammonium bicarbonate pH 8 containing trypsin (2 pmol/µl) (Promega modified trypsin). Additional 10 µl of digestion buffer without trypsin was then added. After incubation at 37° C. for 20 hours, the condensate was collected by spinning the tubes briefly and excess liquid was removed into a new tube. Peptides remaining in the gel matrix were extracted twice with 150 µl 60% aqueous acetonitrile, 0.1% TFA at 30° C. for 30 min. The extracted volume was reduced to about 5 µl using an Eppendorf speed-vac concentrator.

Electrospray Mass Spectrometry

Mass spectrometric data regarding tryptic peptides from in-gel digestions were obtained from collision induced dissociation (CID) spectra with a Finnigan-MAT LCQ ion trap mass spectrometer after introduction via a polyamide coated fused silica microcapillary HPLC.

Immunoblot Analysis of Cytokeratin 1 and Annexin I

Two 2D gels were run simultaneously, both containing identical amounts of lysates of microdissected tumor from case #1. One gel was silver stained and the other was immunoblotted to PVDF membrane as outlined above. 2D western blot analysis was performed as described earlier except antibody to type II cytokeratin or annexin I was used as probe. Anti-pan type II cytokeratin antibody was purchased from SIGMA and used at a final dilution of 1:1000.

Anti-annexin I antibody was purchased from Transduction Labs and used at a final dilution of 1:5000.

Tissue Fixation/Embedding

A male BALB C mouse was sacrificed with immediate surgical excision of the liver. One piece was embedded in OCT compound (Tissue Tek, Miles, Elkhart, Ind.) and immediately frozen on dry ice. Two pieces were fixed in 70% ethanol containing proteinase inhibitor (Complete, Mini Boehringer Mannheim Corp., Indianapolis, Ind.) for 1 hour at room temperature. One of these pieces was then embedded and blocked in paraffin wax and the other in polyester wax (Gallard-Schlesinger Industries, Inc., Carle Place, N.Y.). For the polyester wax embedding the tissue was dehydrated in 90% ethanol at 40° C. for 1 hour followed by 99% ethanol at 4° C. for 1 hour, then by 100% ethanol at room temperature for 1 hour. Then the tissue was infiltrated with 50% polyester wax:ethanol at 42° C. for 2 hours followed by 90% polyester wax: ethanol for one hour at 42° C. Finally, the tissue is blocked with 90% polyester wax: ethanol in a cryomold on ice. A separate piece of liver was fixed in 10% neutral buffered formalin and embedded and blocked in paraffin wax. Eight micron thick sections were cut from each of the blocks onto glass slides, stained with hematoxylin and eosin, and approximately 5000 cells (1200 laser pulses) were dissected by LCM. The transfer cap with attached cells was applied to an Eppendorf tube containing 30 microliters of SDS buffer to lyse the cells, and the recovered protein analyzed by SDS-PAGE.

Protein Profiles of Matched Normal and Tumor Esophageal Cells

Figure 6:
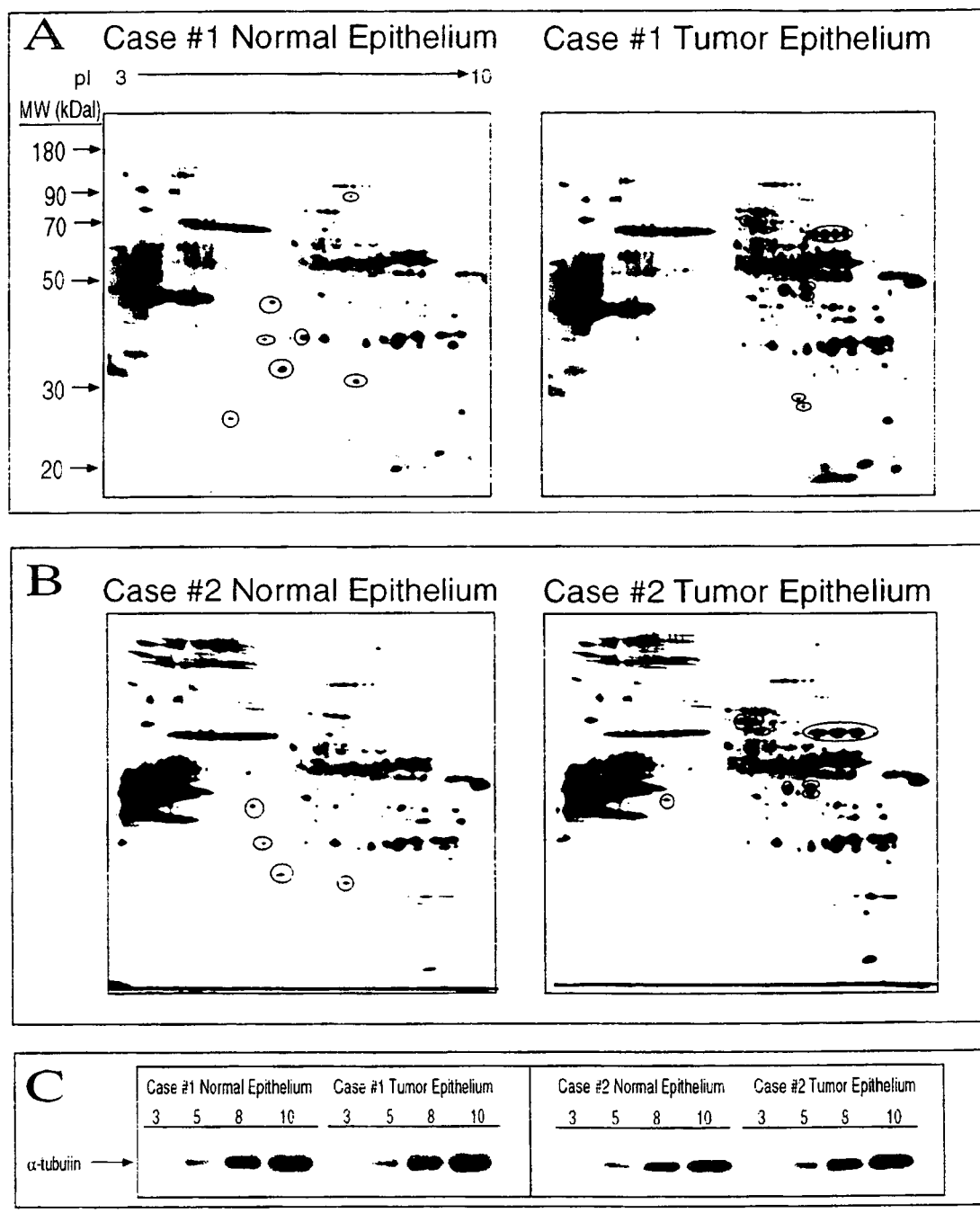

Protein profiles from microdissected normal epithelium and tumor cells from two patients were analyzed by 2D PAGE (FIG. 6). For the purposes of this study proteins were scored as "altered" only if there was a clear-cut "on-off" difference between the comparison groups. No quantitative evaluation was made of the level of those proteins which were present in both sample groups and showed subtle differences in levels. Immunoblot analysis of alpha-tubulin using a small aliquot of each sample was used to verify that equal amounts of total protein were analyzed from each dissection (FIG. 6C).

The overall protein profiles between the normal-tumor pairs were highly similar. For example, the microdissected normal epithelium from case #1 shared 98% of the observed proteins with the corresponding tumor (Table 2).

TABLE 2

|  | # Protein Alterations |
| --- | --- |
| Case #1 Normal epithelium vs. Case #1 Tumor | 15 (2%) |
| Case #2 Normal epithelium vs. Case #2 Tumor | 14 (2%) |
| Case #1 Normal epithelium vs. Case #1 Stroma | 525 (78%) |

Figure 8:
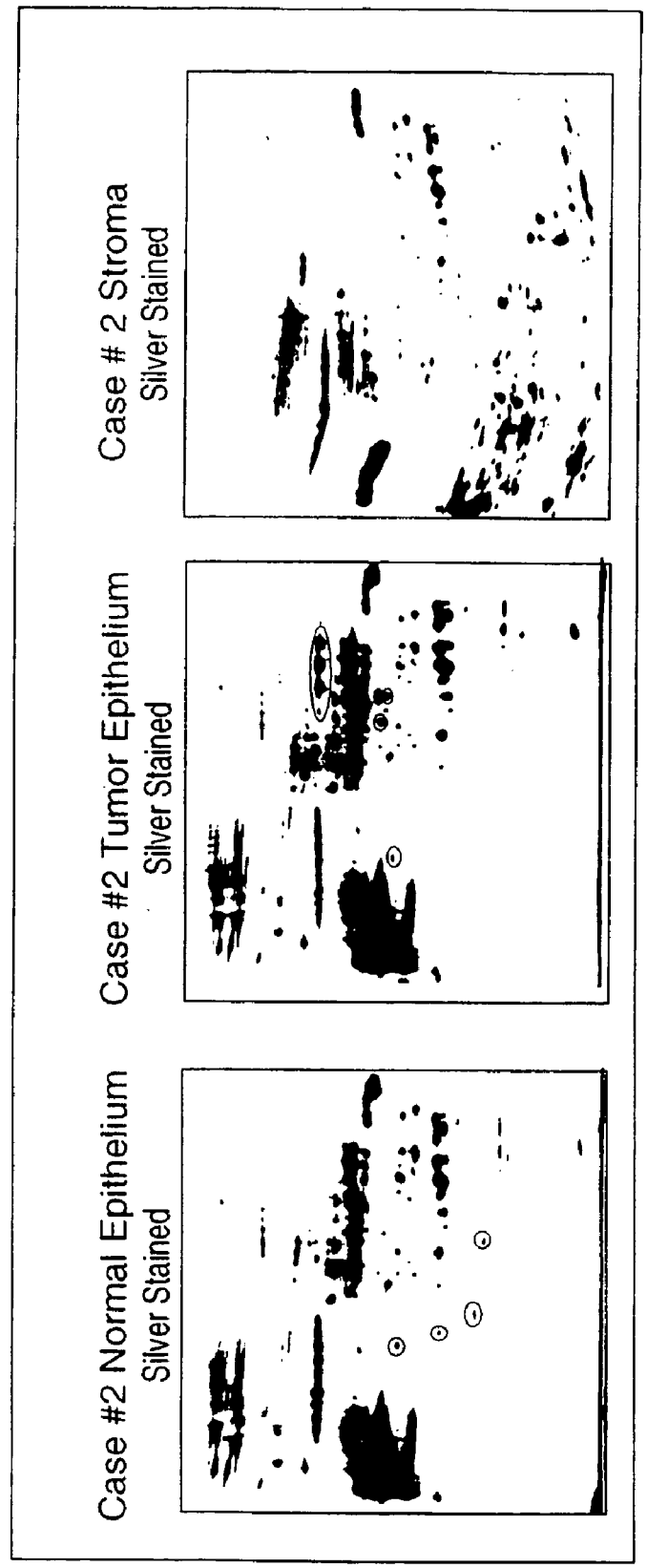
FIG. 8 is a 2-D gel comparison of microdissected normal, tumor epithelium, and stroma tissue indicating the differences by circling the altered proteins. The gels were prepared and run as described in connection with FIG. 6.

However, seventeen distinct differences were observed between the paired normal-tumor samples, 12 of which occurred identically in both cases. The circled spots in panels A and B of FIG. 8 show proteins which are either up or down-regulated in each tumor as compared to the matching normal epithelium. As a control to assess inherent 2D PAGE variability each experiment was performed twice and the results compared. One hundred percent of proteins were scored as identical in each duplicate run (results not shown).

Protein Identification

Two proteins, one overexpressed and the other underexpressed in both tumors, were selected for further analysis to determine the feasibility of obtaining identification of proteins derived from microdissected cells. Spots on the 2D gel marked were chosen for mass spectrometry MS-MS sequencing. A second 2D PAGE gel was run except the gel was stained and analyzed with zinc-imidazole followed by protein elusion and in-gel digestion with trypsin. The volume ratio of trypsin to gel plug was strictly controlled to maximize digestion. In addition, the volatile salt ammonium bicarbonate in the digestion buffer was mostly removed before the samples were used without purification to obtain molecular weights by ESI-MS. For each sample, the peptide mass peaks in the ESI-MS spectra were easily distinguished by the impurities and the masses were corrected by using internal calibration standard. With the protocols used in sample handling and MALDI or ESI loading, a large number of authentic peptide mass peaks were present and this made identification by peptide matching computer programs straight forward and very reliable. The results are reported in Table 3. By matching the experimental molecular weights of trypsin digestion products with theoretical predictions, multiple peptides were identified for each of the two proteins, spanning broad regions of the primary amino acid sequence. The protein overexpressed in tumor was identified as cytokeratin 1, and the protein underexpressed in tumors was identified as annexin I.

TABLE 3

| Protein Identity | Mass Found | Mass Calculated | Residues |
|---|---|---|---|
| Keratin I | 1265.0 | 1265.63 | 278–288 |
| | 1358.2 | 1357.7 | 444–455 |
| | 1476.06 | 1475.75 | 212–223 |
| | 1717.94 | 1716.85 | 418–432 |
| Annexin I | 1702.88 | 1703.6 | 128–143 |
| | 1605.96 | 1607.54 | 98–112 |
| | 1550.82 | 1551.46 | 214–227 |
| | 1387.76 | 1388.00 | 58–70 |

Protein Confirmation—Immunoblot

Figure 7:
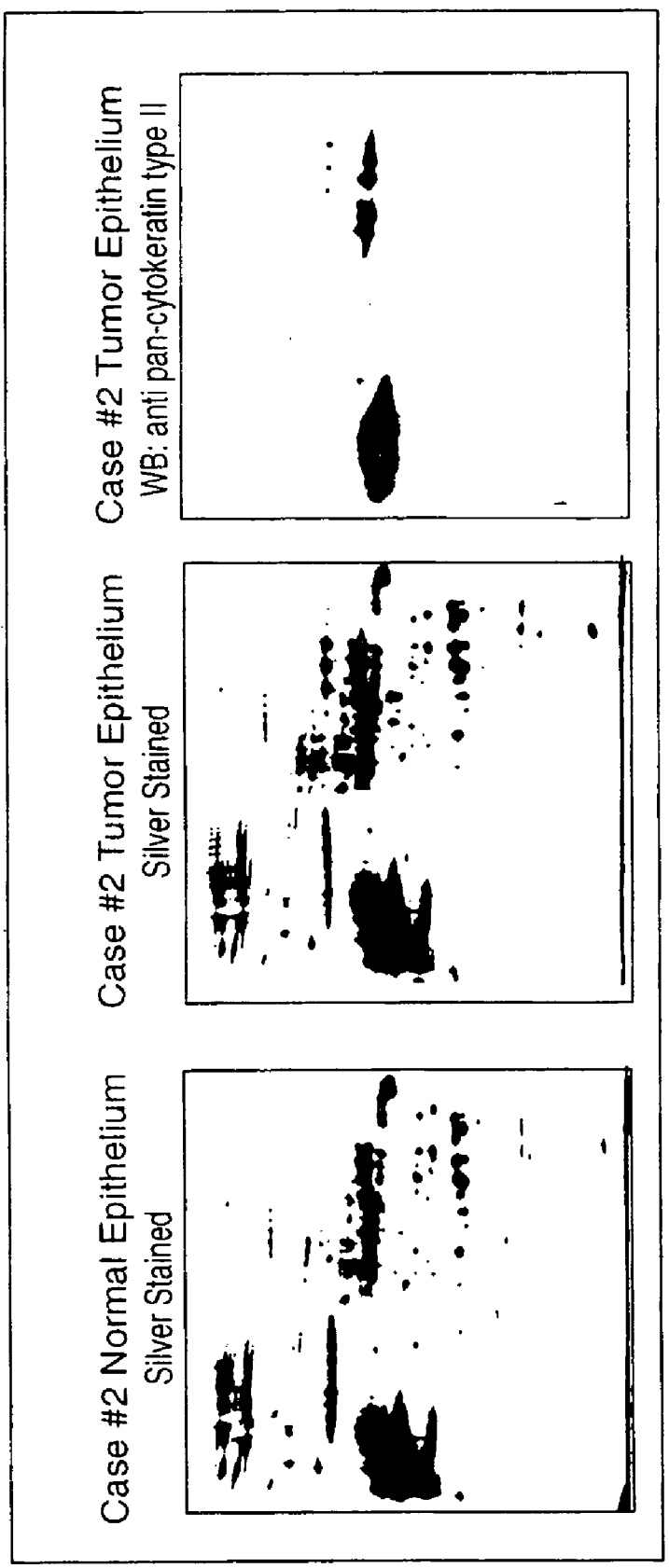
FIG. 7 is a 2-D gel comparison of microdissected normal and tumor epithelium compared to a Western blot using an anti-pan-cytokeratin type II antibody. The gels were run as described for FIG. 6. The completed gel was transferred to PVDF membrane and western blotted with a 1:1000 dilution of anti-pan type II cytokeratin.

To confirm the mass spectrometry results, microdissected normal epithelium and tumor samples from case #2 were subjected to 2D PAGE separation and immunoblot analysis using an antibody directed against a human pan-type II cytokeratin, and an antibody against annexin I. FIG. 7 shows the results confirming the identity of the protein up-regulated in tumor as cytokeratin 1. The identity of the protein down-regulated in tumor as annexin I was similarly confirmed (results not shown). Epithelium vs. Stroma To ensure the present approach is efficient at detecting protein alterations between microdissected cell populations a region of stroma was microdissected and compared to dissected normal epithelium and tumor (FIG. 8). Stroma cells represent a lineage and phenotype markedly distinct from epithelium. Less than 25% (approximately 150 of 675) of the observed proteins were scored as identical between the two populations (Table 2). None of the 17 proteins which were altered in the normal epithelium-tumor comparisons were present in the stroma.

Whole Tissue Sections vs. Microdissected Cells

Figure 9:
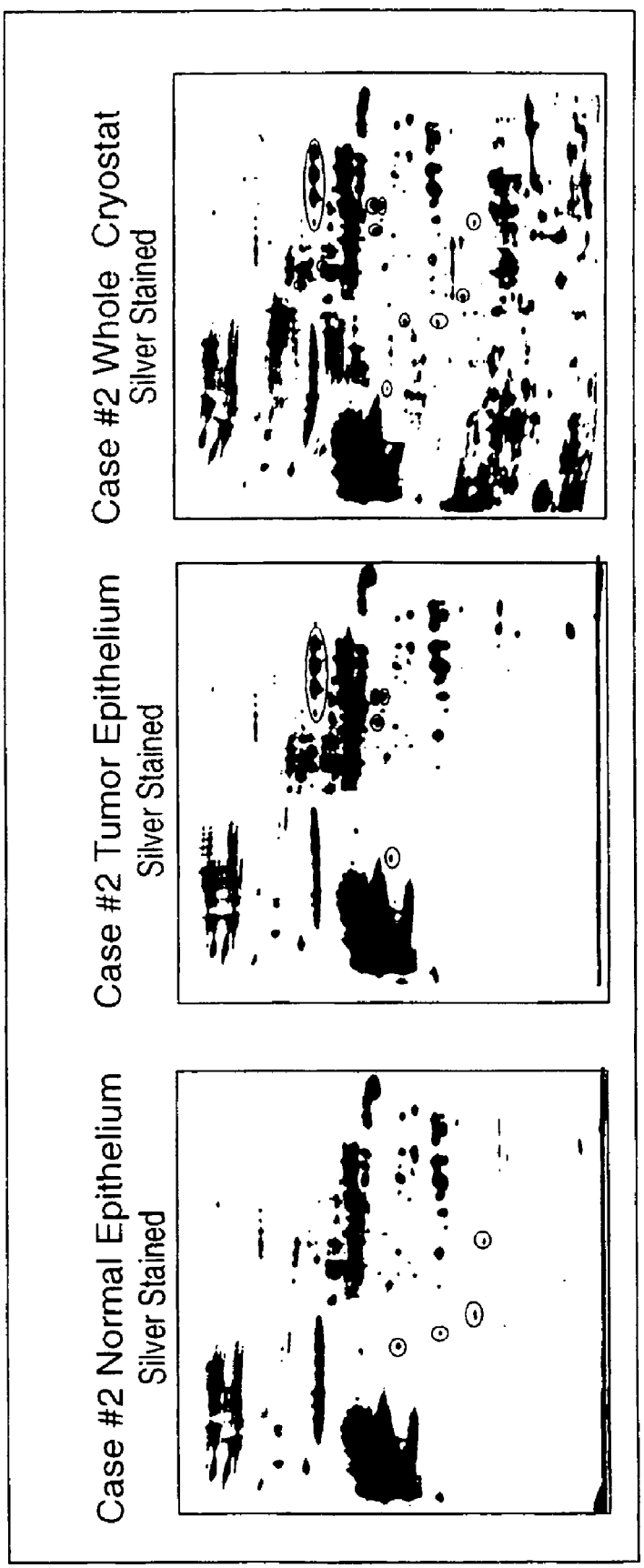
FIG. 9 is a 2-D gel comparison of microdissected normal and tumor epithelium as compared to whole tissue cryostat where circles indicate the locations of the "altered" proteins. The gels were prepared and run as described in FIG. 6.

Samples from whole tissue sections prepared without dissection were analyzed by 2D PAGE and compared to microdissected normal epithelial and tumor cell populations from the same section. The experiment was performed to assess the impact of potential laser capture microdissection induced modifications, such as protein oxidation and proteolysis on 2D PAGE fingerprints. It also determined the percentage of proteins present in a microdissected cell population which could be reliably identified in the whole tissue section from which they were derived. FIG. 9 shows the 2D PAGE comparison of the undissected whole tissue section and corresponding microdissected samples. All of the proteins in the 2D gel from the microdissected cells, including those found to be differentially regulated in the tumor (circled), were visualized at the same Mr and pI in the undissected whole tissue section indicating LCM had no apparent effect on proteins recovered from microdissected cells.

Validation and Extension to Other Cancers

These same methods have been used on eight additional normal/squamous cell cancer of the esophagus cells sets. The results indicated that annexin I is absent in all carcinoma cells, but strongly present in the normal epithelium. Immunohistochemistry experiments, as described above, indicate that annexin I abruptly disappears in this cancer at the pre-malignant state, and continues to be absent as the cells become cancerous. The presently described techniques have also been extended to examine a possible role of annexin I in cancers other than those of the esophagus. In particular, experiments were preformed to determine if the level of annexin I was altered in prostate cancer. Using Western blot analysis and immunohistochemical assays, as described above, 2 of the 3 prostate cancers were found to have completely lost the expression of annexin I, while the third cancer had reduced expression. Thus, these results indicate the applicability of the present techniques to the elucidation of protein alterations in a variety of cancer types and other biological conditions (such as normal organ development).

Previous studies of microdissected cell populations have focused primarily on DNA and more recently on analyses of messenger RNA, and have been aimed at identifying gross genomic alterations, specific genes with mutations, or mRNA levels. While these efforts have been successful and hold great promise for identifying molecular profiles in normal and diseased cells, they provide only partial information regarding the protein products of mutated or dysregulated genes. Efficiency of translation, post-translational modifications, protein stability, phosphorylation state, protein-protein interactions, and protein DNA-binding affinities are examples of parameters which cannot be studied by DNA and mRNA efforts alone. Protein-based analyses are required to address these questions. Moreover, protein profiling may more easily detect certain types of alterations than genomic or expression-based approaches, for example, a tumor suppresser gene mutation which results in protein truncation. Therefore, high-throughput protein studies will be an important component of future efforts to determine the molecular anatomy of normal and diseased cells.

Precise recovery of specific cell populations from human tissue is technically challenging, particularly when downstream molecular applications require on the order of tens of thousands of cells. In this study, procurement of normal epithelium was the most difficult challenge. LCM-based microdissection was critical and allowed recovery of 50,000 normal epithelial (and tumor cells) with a high degree of purity in a reasonably short period of time and did not appear to damage or degrade proteins. Fifty thousand microdissected cells revealed approximately 675 distinct proteins as visualized by 2D-PAGE stained with silver. Assuming the lower limit of detection to be one nanogram, the analysis identified proteins in the abundance range of 50,000 to 1,000,000 copies per cell.

Dysregulated proteins of high or moderate abundance will have sustained utility for basic research and clinical applications as they will be the easiest to detect, study, and monitor. However, proteomic studies of microdissected normal and tumor cells will also benefit from increased sensitivity enabling a larger percentage of the cellular proteins to be analyzed. Additionally, there are many microscopic, biologically interesting (and potentially clinically important) lesions which consist of less than 50,000 cells. In these circumstances, protein labeling with (for example) 125-I labeling or biotinylation dramatically increases the number of proteins visualized from microdissected cells (data not shown). Similarly, scanning immunoblotting with class-specific antibodies allows for more sensitive detection of specific subsets of proteins, for example, all known proteins involved with cell cycle regulation.

In some circumstances, the small amount of material analyzed is not ideal for obtaining highly sensitive protein fingerprints, and identifying proteins of interest. In such circumstances, a useful strategy is to produce parallel "diagnostic" and "sequencing" 2D gels from each case. The diagnostic fingerprints are derived from microdissected cells and provide maximal sensitivity for detection of normal-tumor differences. Sequencing fingerprints then allow for determination of protein identity. The sequencing 2D gels are generated from serial, whole tissue section cryostat recuts which contain abundant amounts of protein representing all cell types present in the tissue, including the dissected cell population(s). Alignment of the diagnostic and sequencing 2D gels permits determination of proteins of interest for subsequent mass spectrometry or N-terminal sequence analysis. This technique successfully visualized and aligned all 675 proteins present in the microdissected tumor cells from case #1 in the corresponding whole tissue section 2D gel. Two of the tumor-specific alterations were selected for subsequent mass spectrometry and identified as cytokeratin I (overexpressed) and annexin I (underexpressed). The identity of both proteins was confirmed by immunoblot. Consistent with this result cytokeratins and annexin I have been previously reported to be dysregulated in epithelial tumors.

It is therefore advantageous, in some embodiments, to compare matched normal and tumor cells from the same patient. Of the seven proteins found to be down-regulated in the tumor, two were observed uniquely in the normal epithelium of case #1, and one was present uniquely in case #2. These proteins are "patient-specific" and would not have been identified if a single reference normal sample had been used as comparator for the tumors. Therefore, direct intra-patient comparison of normal-tumor pairs is advantageous to ensure detection of all protein alterations which occur during tumorigenesis. Moreover, since little is known of the similarities and differences in protein profiles from person to person, the present invention can be used to provide inter-patient analyses of both normal and diseased cells to help reveal patient-unique protein profiles related to disease susceptibility or progression.

The esophageal specimens utilized in this study were frozen in liquid nitrogen shortly after surgical resection and histologic tissue sections were prepared on a cryostat. Frozen sections are often used for molecular analyses of tissue due to the relatively high quality DNA, RNA, and proteins which can be recovered. Tissue processed through standard formalin fixation and paraffin embedding is less advantageous due to the molecular cross-linking which occurs during fixation and the prolonged exposure to elevated temperatures during embedding.

In summary, 2D-PAGE protein profiles and subsequent determination of the identity of selected proteins is possible from microdissected cell populations, and is uniquely capable of detecting disease-specific alterations. These techniques and methodologies can determine the abundance and status of proteins in vivo for studying normal cells and their associated pathologies.

EXAMPLE 3

Comparative Protein Analysis of Normal and Cancerous Prostate Epithelium and In Vitro Prostate Cell Lines Patients and Tissue Samples Tissue from prostate cancer patients undergoing radical prostatectomy at the Clinical Center of the National Cancer Institute (Bethesda, Md.) and at the Mayo Clinic (Rochester, Minn.) was used. Tissue from the peripheral zone of the prostate was procured, immediately snap frozen, and stored at −80° C. Matching normal and tumor cell lines were prepared from the prostatectomy specimens obtained at the NCI and immortalized as described by Bright et al., Cancer Res. 57: 995–1002 (1997). LnCaP and PC3 cells were purchased from the American Type Culture Collection (Manassas, Va.). Microdissection was performed and the cells were prepared for 2D-PAGE analysis as described above in Example 2. 2D-PAGE gels were done using alpha-tubulin to normalize the sample load, as described in Example 2. The anti-alpha tubulin antibodies, used at 1:1000, and HRP-coupled rabbit anti-mouse secondary antibodies, used at 1:10,000, were purchased from Sigma (St. Louis, Mo.). Blots were washed using conditions described above and ECL substrate (Amersham, Piscataway, N.J.) was added for chemiluminescent detection via autoradiography on Kodak Bio-Max film. For PSA, anti-PSA antibodies were purchased from Scripps Laboratories, San Diego, Calif.

Protein Profiles of Matched Normal and Tumor Prostate Epithelial Cells Analysis of the microdissected cells from two different cases revealed approximately 750 distinct proteins as shown by silver staining. Altered proteins were scored as discussed in Example 2 and the results are reported in Table 4. Twelve total proteins were altered between the normal and tumor prostate tissue. Six tumor specific alterations were present in both cases. Two proteins were exclusively expressed in the normal cells of both cases. Three other proteins were uniquely expressed by normal cells from one case, while an additional protein was uniquely expressed by normal cells in the other case. These results confirm the ability of the present methods to make meaningful comparisons between the protein content of microdissected cell samples. Other proteins were overexpressed in the cancerous cells, one of which was confirmed by immunoblot to be PSA. Comparison was also made between epithelial and stromal cells, where less than 45% of the proteins were shared. This result confirms that protein expression differs between epithelium and stroma cell types in various tissue types. The six altered proteins in the epithelial cells were all epithelial specific, indicating that the alterations seen were not due to contamination of the normal cells with stromal cell populations.

TABLE 4

|  | # Protein Alterations |
| --- | --- |
| Normal prostate epithelium vs. tumor | 12 (1.6%) |
| Normal prostate epithelium vs. normal stroma | 412 (45%) |

Comparison to Prostate Cell Line Protein Expression

To determine if the protein profiles from prostate cancer cell lines are representative of prostate cancer in vivo, lysates of cells cultured in vitro were subjected to 2D-PAGE and the resulting patterns compared to those of LCM-derived normal malignant prostatic epithelium. The 2D-PAGE pattern of two common cell lines, LnCaP and PC3, were first compared to the pattern of in vivo cancerous cells. Protein expression between the two cell lines was similar, but markedly different from the protein profiles of epithelium in vivo, exhibiting less than 20% identity. To assess whether differences in 2D-PAGE profiles were the result of qualitative or quantitative alterations in expression, immunoblots were done using PSA as a test molecule. PSA was not detected in normal cells, PC3, or a tumor cell line developed from the in vivo dissected tumor cells. In contrast, LnCaP expressed PSA, but there was an alteration in the migration, reflective of a qualitative change in the protein. These results indicate that there are both quantitative and qualitative changes in cell expression when comparing immortal and in vivo isolated cells. Finally, a direct comparison between the in vivo tumor cells pre-immortalization and a cell line developed from those tumor cells shows substantial alterations in protein expression. This observation means at least some of the differences in protein expression seen between the LnCaP and PC3 cell lines and the tumor cells reflect of changes in protein expression due to the immortalization process.

EXAMPLE 4

Characterization of PSA Proteins in Tumor and Nontumor Cell Samples

LCM of Benign and Malignant Epithelium

Frozen tissue was obtained from radical prostatectomy specimens and embedded in OCT compound (Tissue-Tek, Miles, Elkhart, Ind.). Eight micron sections were made with a standard cryostat and stained with hemotoxylin and eosin using standard protocols. Benign and malignant histology was identified by a pathologist and LCM was performed to obtain cells from each population by directing the laser at those populations of cells. LCM was performed as previously described, except AEBSF (Boeringer Manheim) was added to the staining baths at a final concentration of 2 mM to inhibit proteases. For 1-dimensional and 2-dimensional electrophoresis analysis 2,000 (approximately 8–10,000 cells) and 5,000 (approximately 20–25,000 cells) 30 micron laser shots of each cell population were used, respectively. Based on careful review of histologic sections each dissection is estimated to contain >95% of desired cells.

Western Blot Analysis of Intracellular PSA

For 1D PAGE analysis, 2X SDS buffer was used to lyse cells directly from the EVA film (from the LCM cap) and the lysates were run on 20% tris-glycine nondenaturing gels and transferred to a nylon membrane using the Novex system. A murine monoclonal antibody purchased from Scripps Laboratories was used as the primary antibody at a concentration of 1:1,000 and a murine horseradish peroxidase tagged antIgG antibody from Sigma was used as the secondary antibody. The ECL reaction was generated by the ultra-ECL from Pierce. Purified free PSA and PSA bound to ACT purchased from Scripps were used as controls. For 2-dimensional electrophoresis (2D PAGE), IEF buffer (7M Urea, 2M Thiourea, 4% CHAPS, 1% MEGA-10, 1% Octyl-b-Glucopyranoside, 40 mM Tris, 50 mM DTT, and 2 mM tri-butyl phosphine (TBP) and 0.5% (v/v) Pharmalytes) was used to lyse cells off the EVA fill and the lysates were used to swell pre-cast immobilized pH gradient strips (18 cm, 3–10 nonlinear from Pharmacia) overnight. First dimensional separation was performed for a total focusing time of 120 kVh. The strips were re-equilibrated with a solution containing SDS and Tris PH 6.9, reduced with DTT (50 mM), alkylated with iodoactemide (2.5% w/v), and directly applied to a 9% isocratic SDS-PAGE gel for electrophoresis overnight at 40 volts constant voltage. The protein was transferred to a nylon membrane and western blot performed using previously described reagents. Twenty 8 micron cryostat sections containing both malignant and benign epithelium were suspended in EF buffer and analyzed by 2D PAGE and western blotting as just described.

PSA/ACT binding studies.

Malignant and normal prostatic epithelium were dissected using LCM and lysis buffer (containing protease inhibitors and 100 mM NaCl) was used to lyse the cells off of the EVA film and solubilize the protein. One microgram of purified ACT (purchased from Scripps) was added to 10 ul of lysis buffer containing 2,000 laser shots (approximately 10,000 cells) of normal or malignant epithelium and incubated for 2 hours at 37° C.

Results

Figure 10:
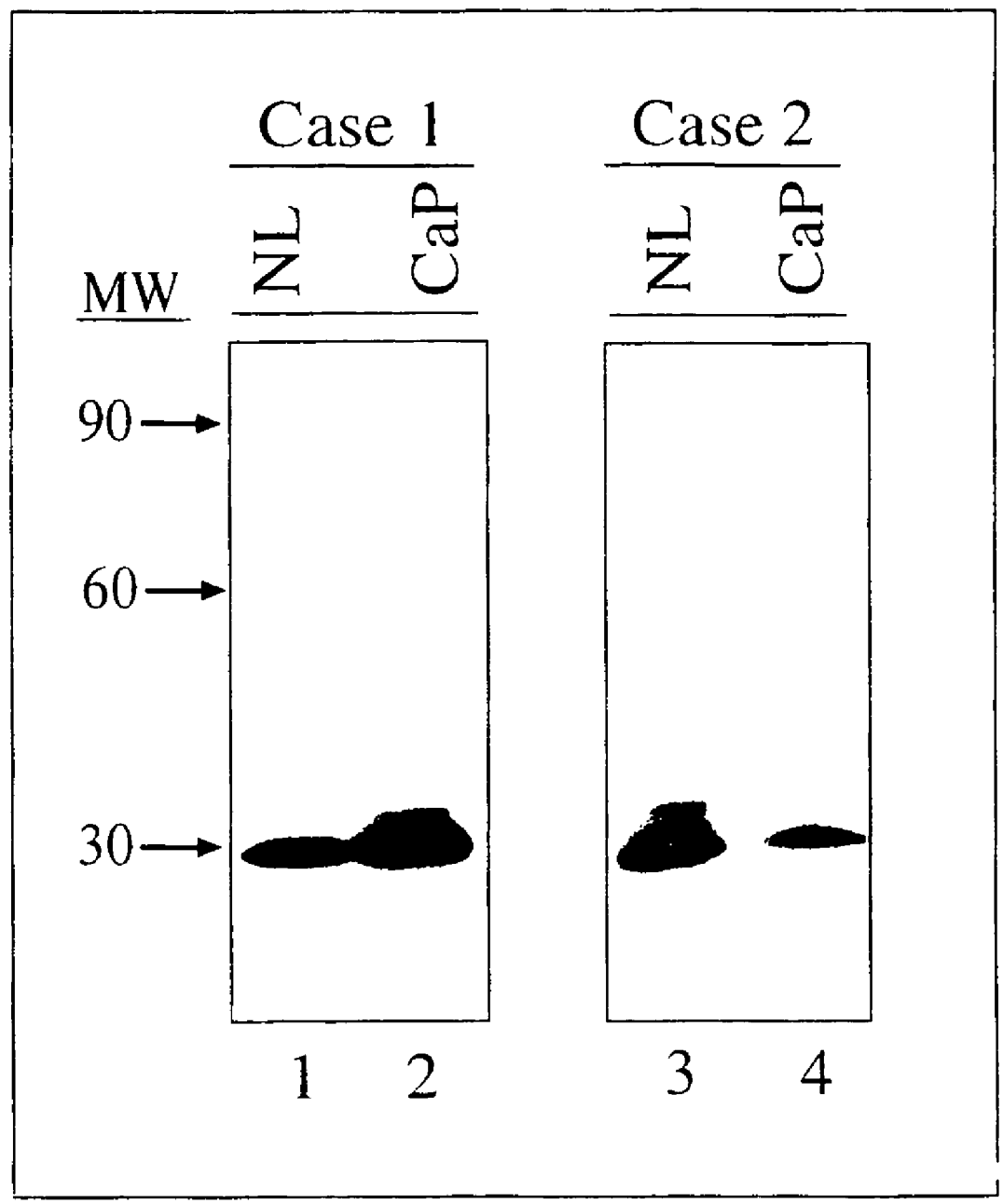
FIG. 10 is a 1D-gel anti-PSA Western blot of cell lysates from microdissected normal and tumor prostatectomy specimens. Lanes 1 & 3 are benign epithelium and lanes 2 & 4 are from malignant epithelium.

PSA is a serine protease that is produced as an inactive zymogen and then activated by release of a signal peptide of 17 amino acids followed by liberation of a 7 amino acid propeptide. The catalytically active form of PSA is highly glycosylated with a molecular mass of approximately 30 kd. Although it has been shown that PSA is constitutively produced in LnCaP cells, the relative proportion of pre and processed forms of PSA within uncultured prostatic epithelium has not been reported. Furthermore, the site at which PSA binds to ACT is also not known. In order to answer these questions, anti-PSA western blot analysis was performed on cellular lysates from LCM derived normal and malignant epithelial cells, which revealed a band at 30 kd (FIG. 10). These results were highly reproducible in several cases and demonstrate that a majority of intracellular PSA exists as a 30 kd form. This finding suggests that PSA binds to ACT within either the extracellular space or the serum and not intracellularly. The total abundance of cellular PSA varied such that in some cases the malignant cells contained more PSA while in other cases the benign cells contained more PSA. This variability of intracellular PSA levels within both normal and malignant prostatic epithelium is consistent with previous reports.

Binding Experiments

Figure 11:
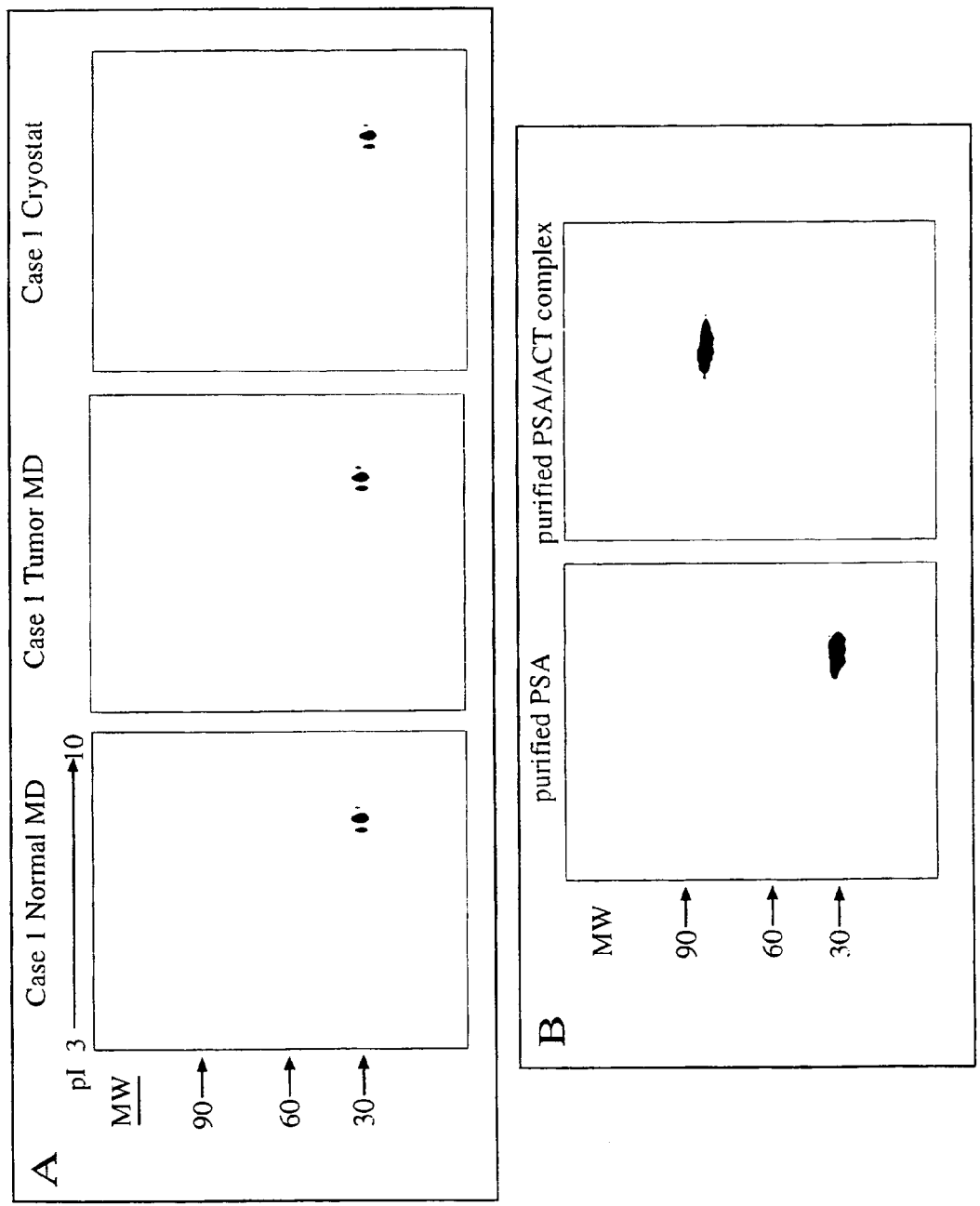
FIGS. 11A and B are anti-PSA Western blots, where lanes 1–4 are benign epithelium and lanes 5–8 are malignant. Lanes 1 & 5 are untreated, lanes 2 & 6 are with ACT added, and lanes 3 & 7 are incubation controls, while lanes 4 & 8 are ACT added with 120 minutes of incubation at 37° C.

To ascertain whether the 30 kd protein represents the active form of PSA we performed experiments to determine if it would bind to ACT. As shown in FIG. 11, the majority of cellular PSA complexed with ACT after 2 hours of incubation and there was no difference in the binding capacity of PSA derived form normal and malignant epithelium. This finding suggests that the 30 kd form represents active PSA but does not explain why serum percent free PSA is lower in men with cancer. Although the PSA found intracellularly in normal and malignant epithelial cells appeared identical by molecular weight and ACT binding capacity, other protein modifications that do not alter patterns on 1D PAGE gels may have been missed by this investigative methodology. Therefore, 2D PAGE was performed on cellular lysates from LCM derived tissue. As can be seen in FIG. 12A, three distinct 30 kd PSA isoforms similarly exist in benign and malignant epithelial cells indicating that the PSA found in malignant prostatic epithelium is not mutated or differentially glycosylated, because this would be reflected in a change in isoelectric focusing point on a 2D Western. Furthermore, none of these three isoforms are a proteolytically cleaved form of PSA since all remained intact under reducing conditions. The fact that the purified PSA/ACT complex remains intact under the reducing conditions (FIG. 12B) validates that the findings demonstrated in FIG. 11 are not an artifact of 2D-PAGE. In addition, whole tissue frozen sections were analyzed (that had not been exposed to LCM) containing both benign and malignant epithelium to demonstrate that firing the laser on the cells did not alter PSA structure (FIG. 12A).

These experiments show that PSA made in normal and malignant prostatic epithelium does not differ in regards to molecular weight, iso-electric focusing point or ability to bind ACT, and that differences in serum percent free PSA levels are not the result of altered ACT production by malignant prostatic epithelium.

EXAMPLE 5

Production of SELDI Protein Fingerprints for Tumor and Nontumor Cell Samples

To assess the reproducibility of the protein fingerprint generated by SELDI, two separate cell populations of prostatic tumor epithelial cells (1200 cells per dissection) from the same patient (Case 1) were separately microdissected (Microdissections 1 and 2) from frozen tissue sections. AEBSF (Boehringer Mannheim) was added to the staining baths at a final concentration of 2 mM to inhibit proteases. Based on careful review of the histologic sections by a pathologist, each microdissection was estimated to have greater than 95% purity. Microdissected cells were lysed directly on an LCM cap with 2 µl of an extraction buffer containing 1% (w/v) Triton-X-100 (Sigma, St. Louis, Mo.), 1% (w/v) MEGA 10 (ICN, Aurora, Ohio), and 1% (w/v) octyl-B-glucopyranoside (ESA, Chelmsford, Mass.) in a standard 1X PBS base. SELDI analysis was performed using an aliphatic reverse phase chip (Ciphergen, Palo Alto, Calif.). The bait surfaces on the chip were pretreated with 2 µl of acetonitrile (Sigma, St. Louis, Mo.). Shortly before the acetonitrile completely evaporated, 2 µl of the lysate was applied to the bait surface. The analyte was allowed to concentrate by air drying followed by the application of 0.3 ml of 3,5-dimethoxy-4-hydroxycinnamic acid (sinapinic acid, 98%, Sigma, St. Louis, Mo.) as the energy absorbing molecule of choice for all experiments in this study.

Figure 13:
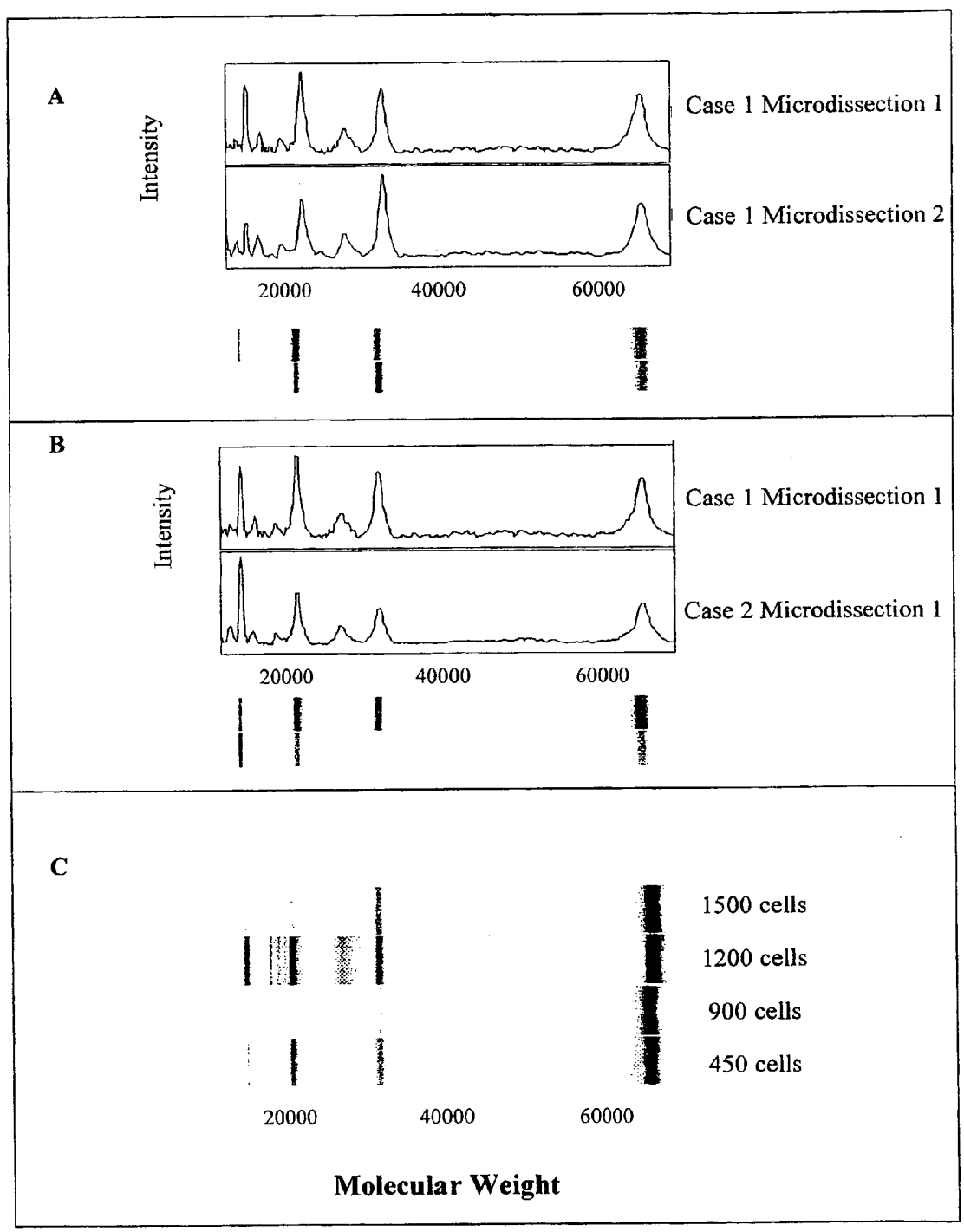
FIGS. 13A, B, and C show data which indicates SELDI protein profiles of LCM-derived cellular lysates are reproducible and sensitive.
FIG. 13B shows two separate microdissections of prostate tumor epithelium from a tissue section from two different patients (1200 cells each) which were analyzed by SELDI protein fingerprinting. The raw mass spectroscopic mass map is shown for each microdissection along with the Gel-View® display from the same data set.
FIG. 13C shows four separate microdissections of decreasing number of cells that were analyzed by SELDI protein fingerprinting. The Gel-View® display is shown as a representation of the direct alignment of each of these four mass spectra to each other.

The results of this experiment (FIG. 13A) are displayed in two of several possible formats offered by the SELDI software analysis package. The first representation is a standard chromatographic mass map with the respective molecular weight range displayed on the x-axis. Each "peak" represents a protein isoform with a different molecular weight. The second representation is a Gel-View® display which takes the peak data from the mass-map chromatogram and presents the data as if one is looking at a standard 1D PAGE gel "stained" for proteins, with the molecular weight ranges displayed at the same scale as that seen in the chromatogram. The protein profiles of the lysates of separate microdissected regions of the same tumor are nearly identical. These results indicate that reproducible protein profiles are generated from LCM-derived cells. Similar experiments were repeated several times with identical results (data not shown).

To assess the reproducibility and relative homogeneity of captured cell populations of the same cell type between patients, prostatic tumor epithelium from two different patients (Case 1 and Case 2) was dissected (1200 cells per dissection) and analyzed as above. These results are shown by both massmapping and Gel-View™ display in FIG. 13B, and show that the protein fingerprint generated from case 1 and case 2 is highly reproducible. Similar results were obtained with multiple samples from the two cases (data not shown). The minor differences in protein expression patterns observed between case 1 and case 2 were no more variable than that seen between microdissections from the same case (data not shown).

To assess the relative sensitivity of the SELDI instrument in the detection of protein profiles from LCM-acquired cells, four separate microdissections of decreasing numbers of prostatic tumor epithelium were isolated and the resulting lysate subjected to SELDI analysis using the reverse-phase aliphatic chip as above. The results shown in FIG. 13C in Gel-View™ display, indicate that a protein profile from as little as 450 cells can be visualized, and that the spectra is comparable to that seen from 1500 cells. The mass maps from fewer numbers of cells (300 and 150) gave less reproducible results, reflecting microheterogeniety in protein expression from region to region in the same tissue section, or indicating that such lower numbers of cells may not provide the most optimal results when assessing complex protein mixtures from small numbers of cells (data not shown). As a control for each experiment, lysing buffer alone, or LCM with a blank glass slide were analyzed. Each produced a flat baseline SELDI spectra (data not shown). The Gel-View® display normalizes the relative intensities of each separate spectra and does not reflect what was seen in the mass map; that is, as the total number of cells decreases, so does the relative intensity of the peaks seen (data not shown). The results using a range of cell numbers indicate that the relative intensity of the peaks may be proportional to the number of cells, the relative fidelity of the spectra is not altered when studying the protein fingerprints of 450 cells to 1500 cells.

For the purposes of these studies only the molecular weight range of 15 kDa to 70 kDa was analyzed, although the SELDI has a practical resolution and detection working range of 1000 to 300,000 daltons depending on the energy absorbing molecule utilized and the bait surface/wash conditions employed. Western blot analysis of LCM derived cells in our laboratory using anti alpha-tubulin as a housekeeping marker for a protein expression reference standard indicated that procurement of cells by an equal number of laser shots generates a nearly equivalent (+/−5%) final protein yield (data not shown).

Discriminatory SELDI Analysis of Different Tumor Types

Figure 14:
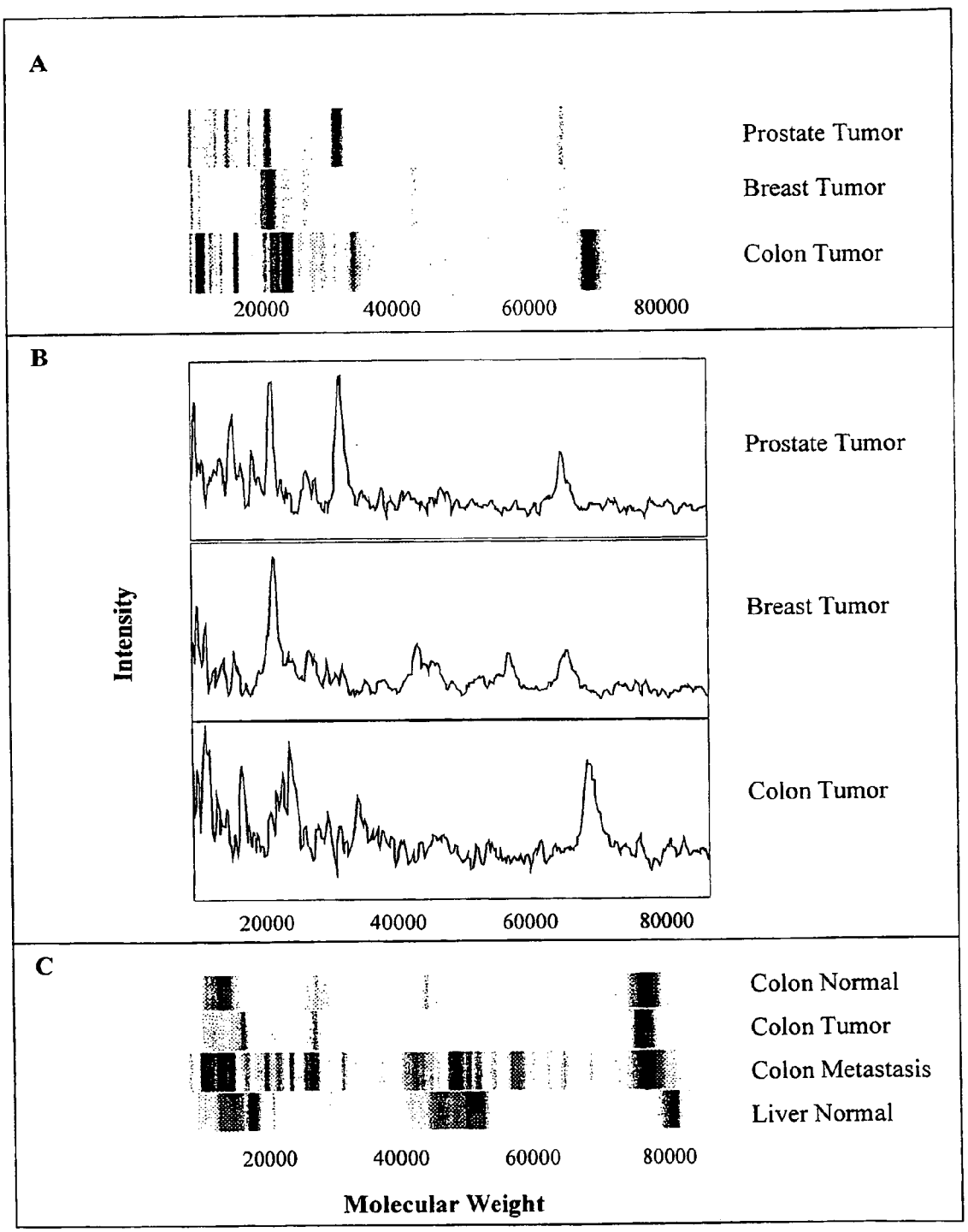

A practical application for both clinical and research studies utilizing SELDI fingerprinting of LCM-acquired cell populations would be to develop diagnostic fingerprints which are disease-specific and organ-specific. To assess the feasibility of this concept, we tested the ability of SELDI to discriminate between tumor epithelium from prostate, breast and colon tumors from different patients. Twelve-hundred cells were analyzed as described above, and the resultant spectra are shown in FIGS. 14A and B. Each tumor type shows a unique fingerprint, illustrating the wide range of protein differences that occur in epithelial cells from different solid tumors types. Novel insights into the protein expression patterns between different types of tumors could aid in the development of new treatment strategies, or the choice of the best strategy. Diagnosis and prognosis from the limiting amounts of cells generated by fine needle aspirants or sentinel node analysis could be achieved very rapidly if a tumor-specific or grade-specific profiles could be generated and used as a template.

SELDI Protein Fingerprinting of Colon Cancer with Liver Metastais

The ability to assess changes in protein expression occurring during tumor progression will aid in the elucidation of the fundamental mechanisms underlying carcinogenesis in patients. To investigate the potential of SELDI analysis of LCM derived cells to study this process, we analyzed the colonic normal epithelium, primary cancer, and hepatic metastasis from one patent. As a comparison, we analyzed the normal liver cells, which were microdissected from the same case. The results are shown in FIG. 14C, and show that a normal epithelial cell and tumor epithelial cell-specific fingerprint can be identified.

Figure 15:
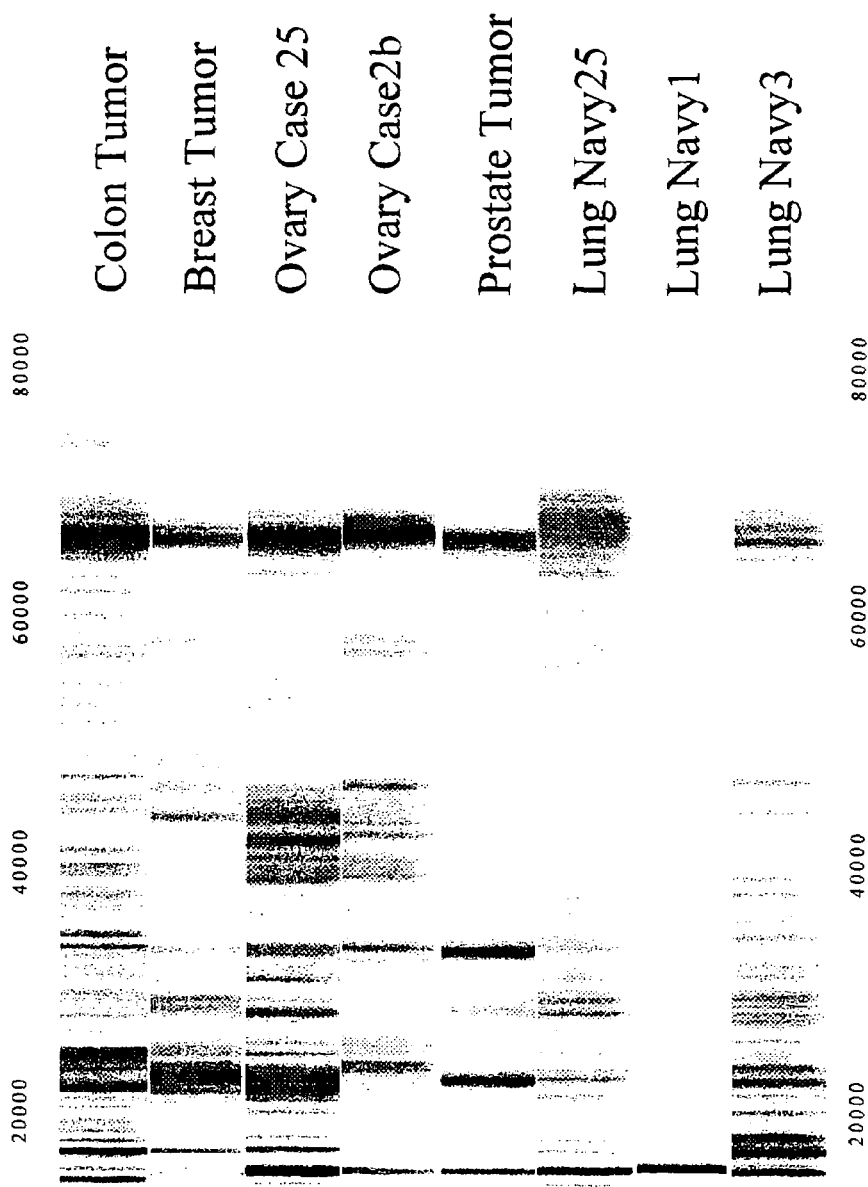
FIG. 15 is a SELDI fingerprint comparison between a variety of tumor types.

Additionally, the protein profile from the colon tumor that had metastasized resembles the colonic epithelium, regardless of tumor or normal cell state, and not the liver cell protein profile. Importantly, the cells from the metastasis have their own distinct protein fingerprint. This uniqueness may arise from the fact that the metastatic tumor has changed its expression profile as a result of its new environment, or it may reflect protein expression changes that enabled the cells to metastasize, or a combination of both. A direct application of this type of analysis would be to identify protein profiles of primary tumors which predict that a tumor has likely metastasized indicating a need for more aggressive patient treatment and follow-up. If the protein fingerprint from the colon to liver metastasis is compared to the fingerprints of the prostate or breast tumor epithelium (FIG. 14A), one can see that the fingerprint most closely resembles that of the colon, regardless of normal or tumor status. A practical application of this type of analysis would be the generation of protein fingerprints that are organ-specific so that metastasis of unknown origin could be characterized and matched to a particular organ type. See FIG. 15 for an example of a battery of fingerprints that could be used.

These results indicate that SELDI analysis of LCM-derived cells can be achieved with a high degree of reproducibility, fidelity, sensitivity and discrimination. These operating conditions allow for the exciting possibility of proteomic analysis of small populations of diseased cells directly from patient tissue. We were able to, for the first time, visualize disease-specific protein changes occurring in defined patient-matched cells directly from tissue sections.

Evaluation of Cancer Disease Progression

Figure 17:
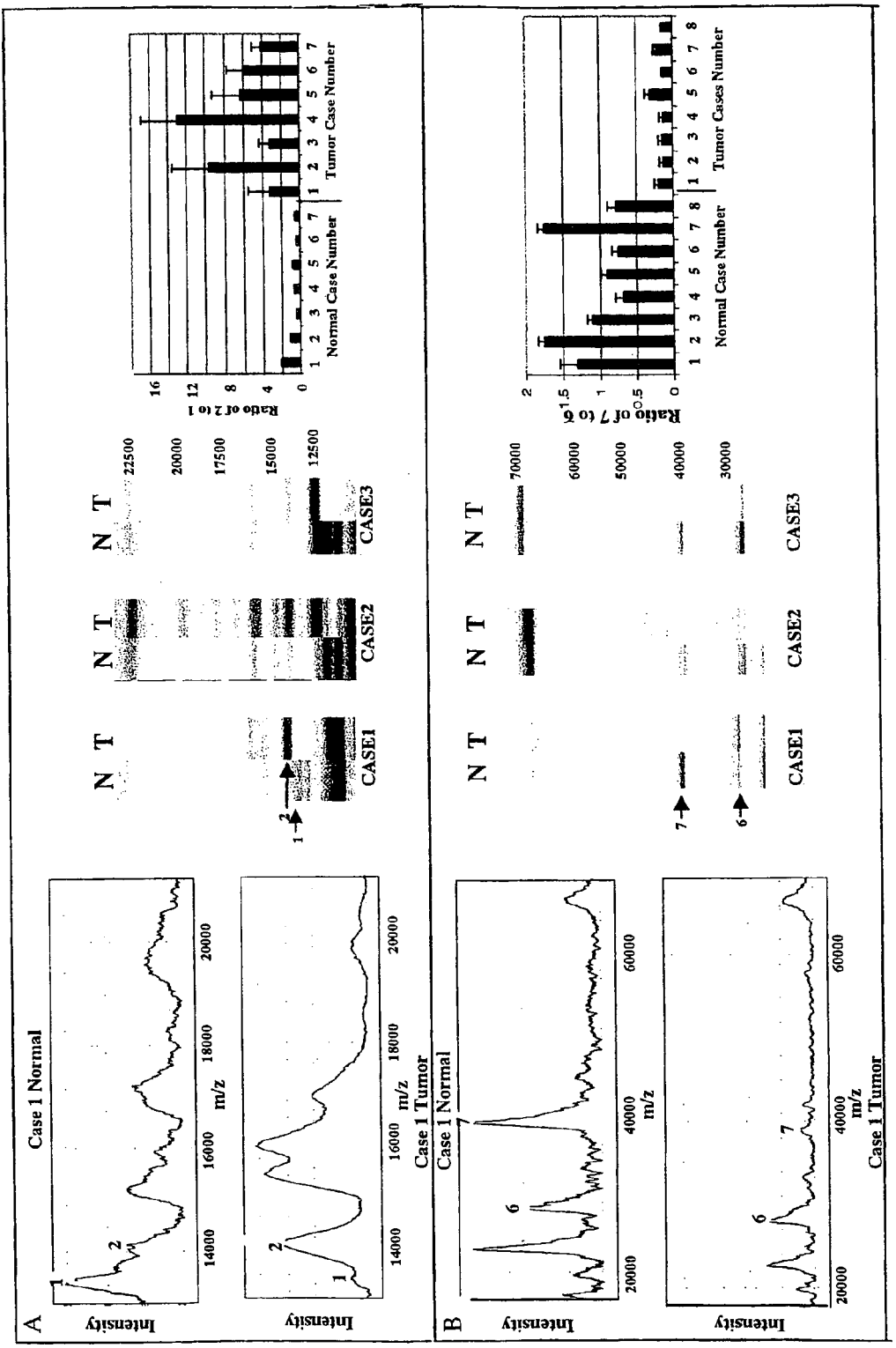
FIGS. 17A and 17B are SELDI analyses of microdissected esophageal epithelium showing proteins disregulated in a disease-specific manner.

Normal, pre-malignant prostatic intraepithelial neoplasia (PIN) and frankly invasive cancer cells and normal cells were microdissected from one stained human tissue section and a protein biomarker fingerprint obtained, as discussed above. The comparisons were made between proteins isolated from approximately 1500 cells and all samples were run in triplicate. Two proteins, having molecular weights of 28,000 and 32,000 Daltons, were found to be reproducibly differentially expressed during the progression of the cells from normal to pre-cancerous to frankly invasive. The results are disclosed in FIG. 17A, 17B, and 17C. In particular, the relative ratio of expression of these two proteins can be correlated to the state of the cell and is reproducible in the three cases analyzed. Although this is an extremely small sample set, this experiment does demonstrate the ability of the present techniques to analysis of the progression of a cell sample to cancer.

Extension to Other Cancers

Figure 18:
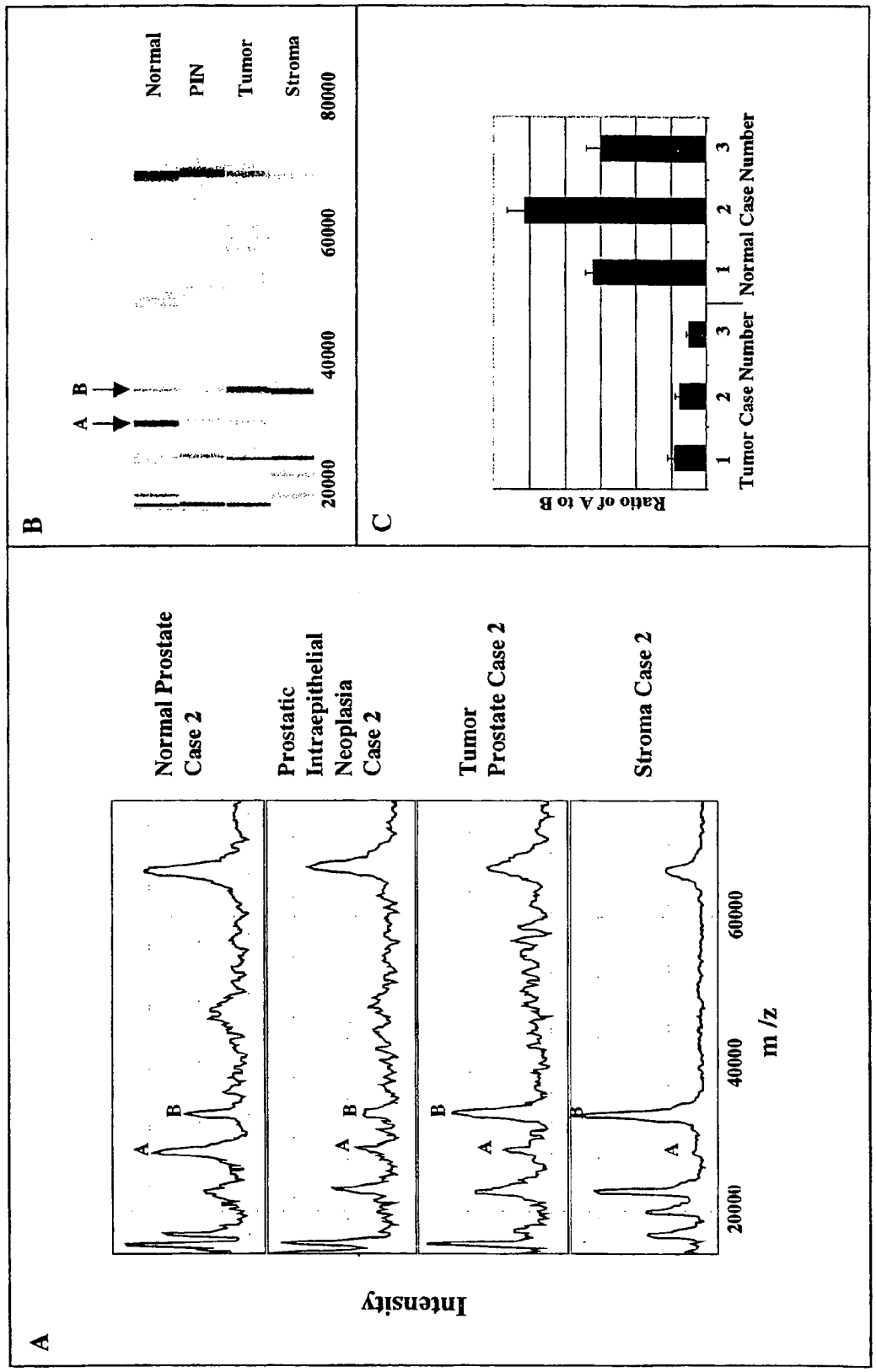
FIG. 18 shows the SELDI analysis of prostate carcinogenesis.

These same methods have been extended to determine the presence of protein "biomarkers" in eight normal/squamous cell cancer of the esophagus cell sets. Three separate independent microdissections of eight different patients' tumor and normal esophageal epithelium were performed and the whole cell lysate subjected to SELDI analysis via the use of a hydrophobic interaction C18 binding surface. Each replicate was run in triplicate, giving a total of 72 data points for each protein peak analyzed. The results are reported in FIGS. 18A and 18B. Two proteins were found to be present in a disease specific manner, one of which was up regulated in a tumor-specific manner in 7 out of 8 cases analyzed, and one was found to be specifically present in normal epithelium from all 8 cases examined. Coefficients of variation and standard deviations for these analyses indicate that the relative abundance of these two proteins may serve as valid "biomarkers" that correlate with disease. Thus, these results indicate the applicability of the present techniques to the elucidation of protein alterations in a variety of cancer types.

EXAMPLE 6

Multiplexed Tissue Arrays for High-Throughput Target Validation and Drug-Tissue Interaction Assay The ability to compare protein content of finite cell samples as described above can be applied to high throughput assays utilizing tissue arrays. Examples of tissue array techniques that can be used with the protein extraction and analysis methods of the present invention are disclosed in PCT publication WO9944063 and WO9944062, whose disclosures are hereby incorporated by reference. The present methods in a tissue array format are useful for screening potential therapeutic agents and analyzing their impact on very small subsets of cells. In particular, the methods are used to analyze the impact of therapeutic agents on specific cellular pathways, such as signaling pathways. These results can, for example, indicate the efficacy or toxicity of a particular agent on the cell.

To apply the present methods to this type of analysis, the tissue from multiple patients is exposed to the agent to be tested. The exposure can be done in vivo, prior to collection of the sample, or in vitro, after collection of the sample and/or after laser microdissection. In vivo exposure would involve administration of the agent to the subject, while in vitro administration could be administration to cultured cells. Some agents that could be tested include pharmacological agents, imaging agents, labeled proteins, such as ligands, or other agents known to have particular effects on cells, such as cytokines. After exposure, microdissection techniques are used to isolate the cells of interest from the sample, the cells are lysed to allow isolation of the proteins or other cellular components, such as nucleic acids or other subcellular structures, from the sample, and the lysate contents are transferred to a confined zone of a substrate. The lystate contents, or cellular components, are placed in identifiable positions on a substrate, where such positions are confined zones. One example of a confined zone is the coordinates of an array. The array is constructed by applying microspots of the isolated proteins on any suitable matrix, such as nitrocellulose, nylon, or silica.

Figure 19:
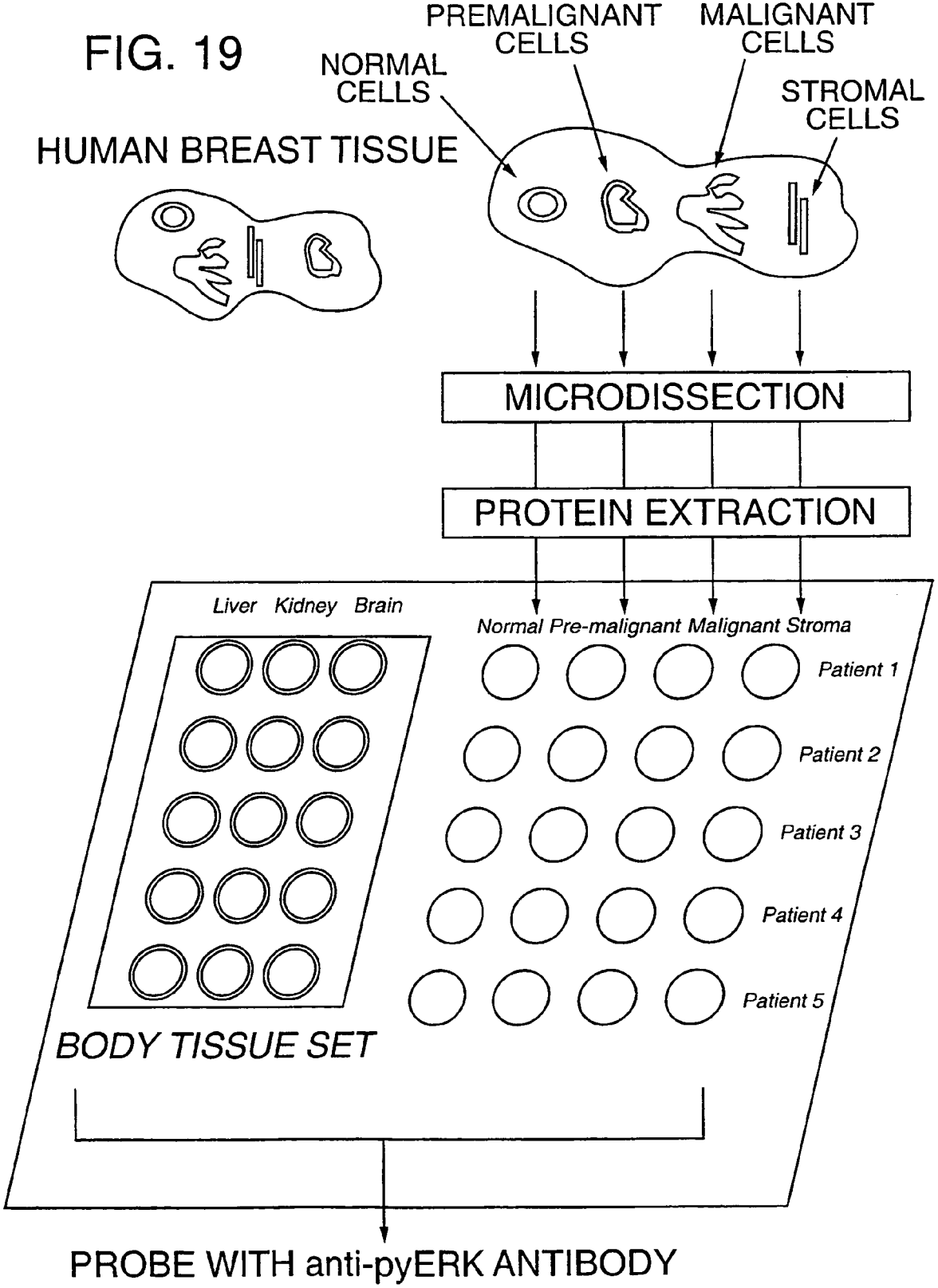
FIG. 19 is a diagram of the multiplexed tissue array method for a high throughput target validation and drug tissue interaction assay, using microdissected human breast cells in various stages of malignancy as an example biological sample.

Referring to FIG. 19, the microspots are arranged on the matrix in any manner that produces meaningful data. The microspots can be placed on the matrix using, for example, a micropipette, and examples of the substrate include a glass or plastic slide, a section of embedding medium, or a nitrocellulose matrix. In one embodiment, the microspots can be arranged in the y-dimension by patient number and in the x-dimension by a criterion for categorizing the various samples obtained, such as by stage of malignancy. Other alternative criteria include before and after treatment samples, various cells types, such as epithelial and stromal, or stages of development for embryonic samples. The microspots are then subjected to some type of analysis, for example, to determine if an amount of a particular protein is altered. Such analysis can include probing with an antibody as the binding agent. Alternative analyses include probing with other binding agents such as nucleic acids, labeled or unlabeled DNA or RNA, or aptameric or phage display screening. A consistent alteration in the cellular content of a protein is then correlated to exposure of the tissue or cells to the agent of interest.

The matrix can be a general capture matrix, such that all isolated proteins from the sample are present, or embedded with a specific binding agent that would result in the maintenance of only proteins of interest. In this embodiment, the microdissected proteins in a soluble form can be labeled, for example with a radioactive or fluorescent tag, and capture by the binding agent is detected by the presence of the label. Alternatively, the protein spots themselves can act as a binding agent or attractant for an interaction, such as detection of a labeled target or ligand within the protein spot after treatment with a labeled test solution. Because of the method of isolation of the proteins, the test is highly sensitive, as each spot may be the protein extracted from a pure population of cells from an individual tissue, or a combination of particular populations of interest.

By using samples from multiple patients, the results have greater statistical significance. Alternatively, a large number of samples can be gathered from one patient's tissue or tissues to achieve the desired statistical results. Other sample sources besides patient tissue include formalin and ethanol fixed paraffin embedded stained tissue sections. With such a sample, it is possible to view the stained tissue using microscopy, then microdissect cells from the precise area of the slide of interest for further analysis. The results can then be referenced back to photographs or other records of the slide image.

Additionally, it is anticipated that the tissue arrays can include a body tissue set, which allows comparison of the results obtained from the experimental tissue set to samples from other tissues of the patient's body. Thus, any variation in individual patient protein composition, or any global effect a therapeutic may have, can be taken into account during interpretation of the results. Other possible controls include known protein mixtures applied to the matrix in spots or "spiking" each spot with a positive control.

A schematic drawing illustrating a sample tissue array for examining protein content of breast tissue of multiple patients is illustrated in FIG. 19. In this illustration, the tissue from multiple patients is used to examine the effect of a particular therapeutic agent administered to a subject on protein content of breast tissue in various stages of malignancy, from normal tissue to stromal invasion. These tissues are microdissected from a tissue specimen using LCM. Because of the sensitivity of the test, detailed questions about effects on the level of cellular biochemical pathways in each stage subset can be obtained.

An additional application of tissue array technology to the methods of the present invention is the use of the protein content assay to prescreen various tissue types for the target of diagnostic or therapeutic moieties. In this embodiment, a therapeutic or diagnostic agent is being evaluated for its appropriateness in a patient's treatment. If the target of this agent is known, the presence or absence of this target in various cell types of the patient can be tested. Thus, using the breast tissue of FIG. 19 as an example, if it was questionable whether a target enzyme for a chemotherapeutic agent was present in a particular patient's cancerous cells, the samples are generated and placed in an array as illustrated. Then an antibody or other means of identification of the target is used to determine if the target agent is present. This allows diagnostic, imaging, or therapeutic agents to be specifically selected for patients or disease types based on the presence of the target molecule in the diseased tissue.

To prepare a comparison assay between a tissue sample and the results of an array analysis, tissue may, for example, be preserved by fixation in 70% ethanol and embedded in a paraffin block. The paraffin block is cut in 5 to 10 um sections and mounted on microscope slides. The tissue on these slides is deparaffinized by placing the slide in room temperature xylene for 5 minutes, followed by xylene heated to 70° C. for 5 minutes. The slide is next placed in acetone for 10 seconds, Diff Quick Solution II (Dade Behringer) for 5 seconds, and acetone for 10 seconds. The stained slide is allowed to rinse in xylene for a minimum of 30 seconds to dehydrate.

Cells of interest are dissected from the slide by LCM using the PixCell II (Acturus Engineering). Using the 30 $\mu$m spot size, 3000 laser pulses are fired to collect cells from a subcellular structure of interest, and the cells are embedded in a thermoplastic polymer film supported on a plastic cap. An extraction buffer consisting of one part SDS sample buffer (Novex) with 4% BME and one part T-PER (Pierce) is heated to boiling. A 40 $\mu$l aliquot of the hot extraction buffer is added to a standard 500 $\mu$l microcentrifuge tube. The cap containing the tissue embedded on the thermoplastic film is inserted into the tube and inverted to allow the extraction buffer to cover the tissue. The inverted tube is vortexed for 20–30 seconds to aid in the disruption of the cells and release of the cellular components. Still inverted, with the buffer flooding the cap surface, the tube and cap assembly is placed in a 70° C. incubator for overnight incubation. After the incubation, the tube is once more vortexed in an inverted position, after which it is turned upright and centrifuged for 10 seconds. Dilutions are made from the resulting lysate using T-PER. A minimum of 10 $\mu$l of lysate or dilution is placed in the bottom of a well of a 96-well round-bottom microtiter plate.

This plate is positioned on the stage of Genetic Micro Systems 417 Arrayer. Oncyte Slides (Schleicher & Schuell) covered in pure nitrocellulose are placed in the appropriate positions on the arrayer. After the desired number of slides and replicates has been programmed into the accompanying software, the instrument is activated. A metal micro tube lowers into the appropriate well and lifts 1 $\mu$l of the lysate, trapping it inside the bore of the tube. After positioning the tube over the nitrocellulose slide, a pin pierces the trapped lysate, spotting a minute aliquot onto the nitrocellulose surface measuring 500 µm in diameter.

Two different detection systems have been used successfully to visualize and quantitate the concentration of the proteins applied to the nitrocellulose and are representative of the detection means that can be used with the methods of the present invention.

System One

The Western-Star Chemiluminescent Detection System (TROPIX, Inc., Bedford, Mass.) is an immunoblot detection system designed for membrane-bound proteins. The protocol outlined for nitrocellulose membranes is followed for the Oncyte slides. After the nitrocellulose slide is prepared on the arrayer and dried, it is submerged in I-Block blocking buffer (provided in the kit) prepared as directed, and agitated on an orbital mixer for at least 1 hour. The primary antibody of choice is diluted of the recommended concentration using I-Block buffer. The slides are drained after the blocking step and the diluted primary antibody is poured over the slides and for incubation, with agitation, overnight at 4° C. After the overnight incubation, the slides are washed with agitation in a 1X PBS/0.1% TWEEN washing buffer, one time for 15 minutes and twice for 5 minutes. The secondary antibody which is conjugated to alkaline phosphatase is diluted in I-Block blocking buffer and poured over the slide. It is allowed to incubate for 4–5 hours at room temperature on an orbital mixer. At the end of this incubation, the slide is washed with PBS washing as described above. The 10X Assay Buffer (provided in the kit) is diluted with deionized water and the slide is incubated twice for two minutes submerged in the 1X Assay Buffer. The slides are blotted dry on a piece of tissue paper. For the nitrocellulose slides, a 1:20 dilution of Nitro-Block-II (provided in the kit) is prepared using the CDP-Star Ready-To-Use substrate solution. This substrate solution is pooled on the slide and allowed to sit undisturbed for 5 minutes.

At the end of this incubation, the slide is blotted and placed in a plastic development folder, after which it is exposed to x-ray film. Representative results using this system for analysis of the content of prostate soluble antigen in prostate tissue is shown in FIGS. 20B and 20C.

System Two

The second illustrative example uses the DAKO Autostainer Universal Staining System (DAKO Corporation, Carpinteria, Calif.). This automated slide processing system uses a primary antibody followed by the addition of a patented horse-radish peroxidase labeled polymer (DAKO EnVision™ System). This is an example of a colorimetric-detectable labeled antibody. The prepared Oncyte slide is blocked in I-Block (TROPIX, Inc.) for a minimum of 1 hour. The DAKO Autostainer is programmed with the incubation times and volumes of the reagents to be dispensed on the slides. The nitrocellulose slide is washed with a Wash Buffer wash (prepackaged by DAKO). The primary antibody, diluted as specified for the antibody being used, is applied in the predetermined amount of 600 µl, and allowed to incubate for 30 minutes. At the end of the incubation, the slide is washed with 600 µl of the Wash Buffer. This step is followed by the addition of the HRP labeled polymer for 10 minutes, followed by washing with the Wash Buffer. The substrate is added to the slide and allowed to sit for 5 minutes, followed by a final wash, and is then allowed to dry for optimal visualization. The positive results are visible staining of the spotted proteins on the slide. Representative results using this system for analysis of the content of prostate soluble antigen (PSA) in prostate tissue are shown in FIG. 20A.

The tissue array method for analyzing protein content of small sample sizes is very reproducible, even when applied to very small numbers of cells. Experiments to examine the reproducibility of the technique were done using five separate slides of normal esophageal tissue, and detection for annexin I was performed. The size of the samples varied in the number of microdissection "shots," from a high of 500 shots to a low of 16 shots. Samples of varying cell numbers were collected, the proteins were isolated as described above, and the isolated proteins were placed on a matrix of nitrocellulose paper. Using standard Western techniques, the microspotted proteins were probed using the antibody systems described above. The results of these tests are diagrammed in FIGS. 21A, 21B, and 21C. FIG. 21A indicates that the results from each data set (average of triplicate results for each slide) remains consistent within the set. As is expected, the amount of variance increases with the smaller number of "shots" included in the sample. However, as indicated graphically in FIG. 21B, the results for multiple samples containing as few as 125 shots varies only by 18%. These results indicate that this method of analyzing protein content of small tissue samples is reliable. The results shown in FIG. 21C also support this conclusion and indicate that the relative value between the various series remains generally consistent between samples of varying numbers of shots. In summary, the results indicate that decreasing the number of "shots" in a sample affects only the quantitative, not qualitative, character of the results.

Figure 22:
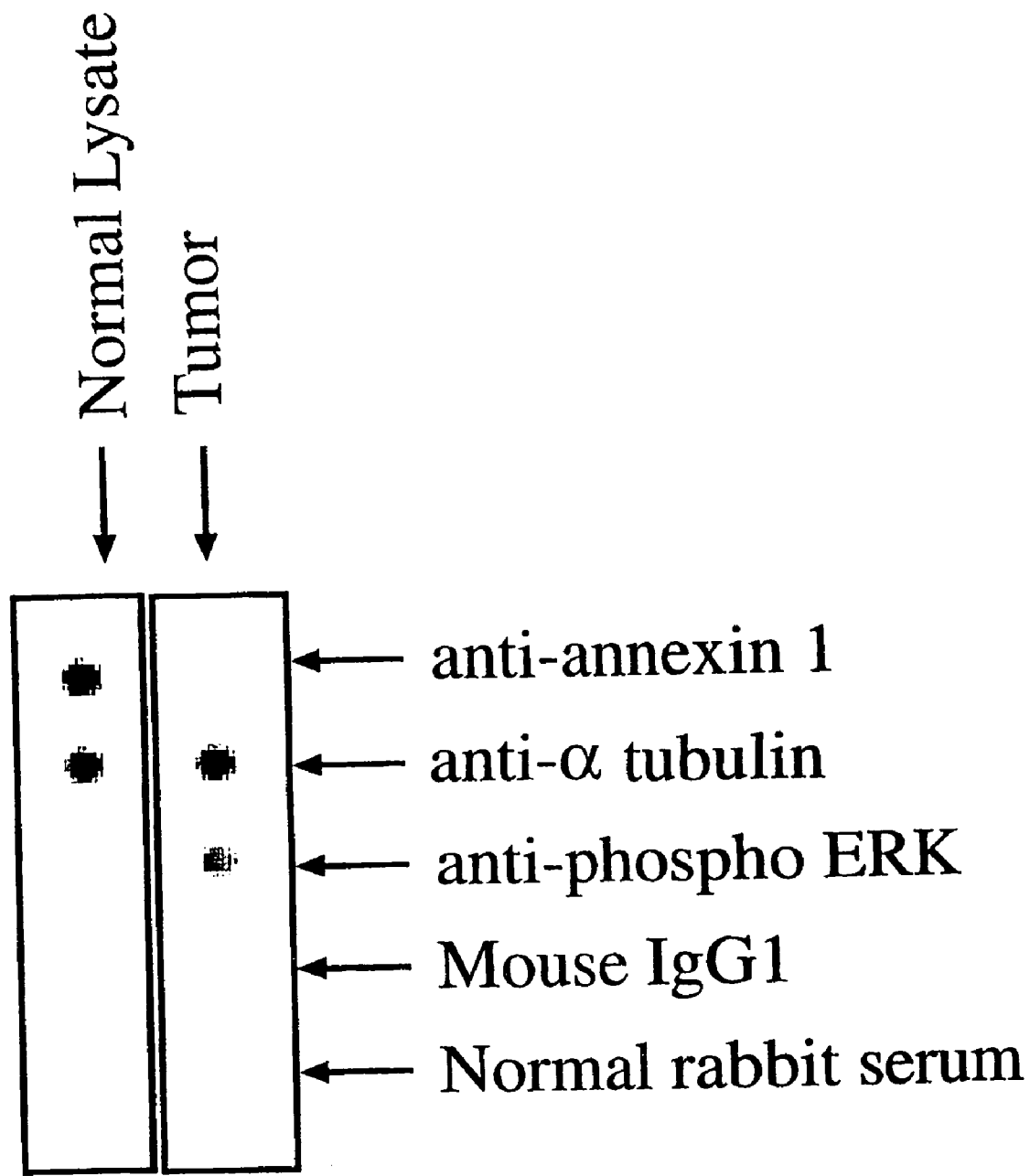
FIG. 22 shows the results of interaction between immobilized binding agents and biotin-labeled lysates from microdissected normal and tumor cells.

Example results of method of present invention where the binding agent has been immobilized, and the cell lysates placed in contact with the immobilized agent are shown in FIG. 22. In this experiment, lysates from microdissected normal and tumor esophageal cells were labeled with biotin. An array of binding agents, including anti-annexin I, anti-alpha tubulin, anti-phospho ERK, and mouse IgG1, and normal rabbit serum were placed on nitrocellulose paper. Biotin labeled lysates were placed in contact with the binding agent arrays, and the interaction was detected by avidin-peroxidase. As shown in FIG. 22, the tumor lysates contained a reduced concentration of annexin I, and an increased concentration of phospho ERK when compared to the normal cell lysates.

It is understood that the invention is not limited to the specific embodiments shown and described, but changes or modifications can be made in the embodiments without departing from the contemplated scope of the present invention.

We claim:

1. A method comprising:
   extracting a population of about 1500 or fewer cells from a tissue sample using microdissection under microscopic visualization;
   isolating a protein sample from the extracted cell population, wherein isolating the protein sample comprises solubilizing contents of the extracted cell population in less than about 20 µl of a buffer; and
   analyzing the isolated protein sample.

2. The method of claim 1 wherein the buffer comprises at least one detergent to solubilize the cellular lipids, at least one proteinase inhibitor to preserve protein content and function, and at least one salt to lyse the nuclear contents.

3. The method of claim 2 wherein the cell contents are solubilized in about 1 µl to about 15 µl of buffer.

4. The method of claim 1 wherein analyzing the isolated protein sample comprises performing a soluble immunoassay using a labeled antibody specific for a protein of interest.

5. The method of claim 4 wherein the labeled antibody is labeled with a marker selected from the group consisting of colorimetric-detectable, chemiluminescence, fluorescence, and radioactivity.

6. The method of claim 1,
wherein extracting the population of cells from the tissue sample comprises laser capture microdissection; and
wherein isolating the protein sample from the extracted cell population comprises solubilizing the extracted cell contents in about 1 μl to about 15 μl of a buffer where the buffer comprises Tris-HCl, NONIDET® P40 (octylphenolpoly(ethyleneglycolether)), sodium deoxycholate, sodium chloride, ethylenediaminetetraacetic acid, aprotinin, leupeptin, sodium pyrophosphate, sodium orthovanadate, and 4-(2-aminoethyl)-bezenesulfonylfluoride; and
wherein analyzing the isolated protein sample comprises performing a soluble immunoassay using an antibody specific for a protein of interest in the isolated protein sample, where the antibody is labeled with a marker selected from the group consisting of colorimetric-detectable, chemiluminescence, fluorescence, and radioactivity, and calibrating the assay to indicate the amount of the protein of interest present in the isolated protein sample.

7. The method of claim 6 wherein the protein of interest in the isolated protein sample is prostate soluble antigen (PSA).

8. The method of claim 1 wherein analyzing the isolated protein sample comprises:
performing a one dimensional polyacrylamide gel electrophoresis (1D PAGE) or two dimensional polyacrylamide gel electrophoresis (2D PAGE) to separate proteins in the isolated protein sample from each other; and
further analyzing the proteins in the isolated protein sample using a protein specific dye or Western blotting with a labeled antibody specific for the protein of interest in the isolated protein sample.

9. The method of claim 1 wherein analyzing the isolated protein sample comprises
performing a two dimensional polyacrylamide gel electrophoresis (2D PAGE) to separate the proteins in the isolated protein sample from each other;
isolating a protein of interest from the gel; and
determining an amino acid sequence of the protein of interest.

10. The method of claim 9 wherein the sequence is determined using a method selected from the group consisting of N-terminal sequencing, mass spectrometry MS-MS sequencing, liquid chromatography quadrapole ion trap electrospray (LCQ-MS), and matrix assisted laser desorption/time of flight analysis (MALDI/TOF).

11. The method of claim 1 wherein analyzing the isolated protein sample comprises performing surface enhanced laser desorption ionization spectroscopy (SELDI) to produce a protein fingerprint for the cell population.

12. The method of claim 1 wherein the cell population is microscopically identifiable as a tumor cell.

13. The method of claim 1, wherein analyzing the isolated protein sample comprises:
performing a one dimensional polyacrylamide gel electrophoresis (1D PAGE) or two dimensional polyacrylamide gel electrophoresis (2D PAGE) to separate the proteins from each other;
removing at least one protein of interest from the gel;
further analyzing the protein of interest by incubating the protein with a known or putative binding partner for the protein of interest; and
determining whether the protein of interest binds to the known or putative binding partner.

14. The method of claim 13 wherein the protein of interest is PSA and the known binding partner is alpha-1-antichymotrypsin (ACT).

15. The method of claim 1, comprising:
extracting at least a first and a second population of cells directly from one or more tissue samples using laser capture microdissection;
isolating protein from the extracted cell populations to generate for each cell population an isolated protein sample having a content;
analyzing the isolated protein sample for at least two cell populations; and
comparing the protein content of the isolated protein sample of at least the first cell population to the protein content of the isolated protein sample of at least the second cell population to identify differing content.

16. The method of claim 15 wherein the buffer comprises Tris-HCl, NONIDET® P40 (octylphenolpoly(ethyleneglycolether)), sodium deoxycholate, sodium chloride, ethylenediaminetetraacetic acid, aprotinin, leupeptin, sodium pyrophosphate, sodium orthovanadate, and 4-(2-aminoethyl)-bezenesulfonylfluoride.

17. The method of claim 15 wherein the cell contents are solubilized in about 1 μl to about 15 μl of buffer.

18. The method of claim 15 wherein analyzing the isolated protein comprises performing a soluble immunoassay using a labeled antibody specific for a protein of interest wherein the assay is calibrated to indicate the amount of the protein of interest present in the sample.

19. The method of claim 18 wherein the immunoassay is of high sensitivity and the labeled antibody is labeled with a marker selected from the group consisting of colorimetric-detectable, chemiluminescence, fluorescence, and radioactive labels.

20. The method of claim 15 wherein analyzing the isolated protein comprises:
performing a two dimensional polyacrylamide gel electrophoresis (2D PAGE) to separate proteins from each other;
isolating a protein of interest from the gel; and
determining an amino acid sequence of the protein of interest.

21. The method of claim 20 wherein the sequence is determined using a method selected from the group consisting of N-terminal sequencing, mass spectrometry MS-MS sequencing, liquid chromatography quadrapole ion trap electrospray (LCQ-MS), and matrix assisted laser desorption/time of flight analysis (MALDI/TOF).

22. The method of claim 15 wherein analyzing the isolated protein comprises:
performing a one dimensional polyacrylamide gel electrophoresis (1D PAGE) or two dimensional polyacrylamide gel electrophoresis (2D PAGE) to separate protein fractions from each other; and
further analyzing the protein fractions using a protein specific dye or Western blotting with a labeled antibody specific for a protein of interest.

23. The method of claim 15 wherein the first population of cells and the second population of cells are from the same tissue sample and the first population is microscopically identifiable as tumor cells and the second population is microscopically identifiable as normal cells.

24. The method of claim 15 wherein the first population comprises several subpopulations wherein each subpopulation is microscopically identifiable as cells at different stages of tumor progression.

25. The method of claim 1, comprising:
extracting first and second populations of about 1500 or fewer cells from the tissue sample using laser capture microdissection, in which a laser targets the first and second populations as microscopically distinct and separates them from a larger microscopic structure; and
isolating a protein sample from each extracted cell population by solubilizing the extracted cell contents in about 1 µl to about 15 µl of a buffer where the buffer comprises Tris-HCl, NONIDET® P40 (octylphenolpoly(ethyleneglycolether)), sodium deoxycholate, sodium chloride, ethylenediaminetetraacetic acid, aprotinin, leupeptin, sodium pyrophosphate, sodium orthovanadate, and 4-(2-aminoethyl)-bezenesulfonylfluoride;
wherein analyzing each of the isolated protein samples comprises:
performing a one dimensional polyacrylamide gel electrophoresis or two dimensional polyacrylamide gel electrophoresis to separate proteins of the protein sample from each cell population;
further analyzing the separated proteins of each cell population using a protein specific dye or Western blotting with a labeled antibody specific for a protein of interest; and
comparing a protein of interest content of the first cell population to a protein of interest content of the second cell population.

26. The method of claim 1, comprising:
extracting first and second populations of about 1500 or fewer cells from the tissue sample and from each other using laser capture microdissection;
isolating a protein sample from each extracted cell population by solubilizing cells from extracted cell populations in about 1 µl to about 15 µl of a buffer where the buffer comprises Tris-HCl, NONIDET® P40 (octylphenolpoly(ethyleneglycolether)), sodium deoxycholate, sodium chloride, ethylenediaminetetraacetic acid, aprotinin, leupeptin, sodium pyrophosphate, sodium orthovanadate, and 4-(2-aminoethyl)-bezenesulfonylfluoride; and
wherein analyzing each of the isolated protein samples comprises:
performing surface enhanced laser desorption ionization spectroscopy (SELDI) to produce a protein fingerprint of the protein sample for each cell population; and
comparing the protein fingerprint of the first population of cells to the protein fingerprint of a known second population of cells to determine whether or not the two populations have the same origin.

27. The method of claim 26 wherein the first population of cells is microscopically identifiable as a tumor metastasis and the second population of cells is one of a battery of known normal tissue samples.

28. The method of claim 27 wherein the known normal tissue samples are from the same patient as the first population of cells.

29. The method of claim 1, wherein isolating the protein sample from the extracted cell population comprises
lysing the extracted cell population to produce cellular components; and
wherein analyzing the isolated protein sample comprises:
immobilizing at least one cellular component or a binding agent in a confined zone;
contacting the cellular components with a binding agent; and
detecting the interaction between the components and the binding agent.

30. The method of claim 29 wherein the cellular component or the binding agent is labeled, and detecting the interaction between the cellular component and the binding agent comprises detecting the presence of the label.

31. The method of claim 30 wherein the label is detected by a method selected from the group consisting of a calorimetric, chemiluminescent, radioactive, and fluorescence.

32. The method of claim 29 wherein the confined zone of the immobilized cellular component or the immobilized binding agent is an array.

33. The method of claim 29 wherein the cellular component is immobilized.

34. The method of claim 29 wherein the binding agent is immobilized.

35. The method of claim 1, wherein analyzing the isolated protein sample comprises generating on a substrate an array comprising a series of at least two dilutions of the protein sample.

36. The method of claim 35, wherein analyzing the isolated protein sample further comprises:
applying a first labeled probe that specifically detects a first protein analyte; and
obtaining a quantitative value for the first protein analyte by comparing a signal from the first labeled probe at different positions in the dilution series.

37. The method of claim 36, further comprising:
applying a second labeled probe that specifically detects a second protein analyte; and
obtaining a quantitative value for the second protein analyte by comparing a signal from the second labeled probe at different positions in the dilution series.

38. The method of claim 6, wherein calibrating the assay comprises generating a serial dilution of the protein sample.

39. The method of claim 15, wherein analyzing the isolated protein sample for at least two cell populations comprises generating on a substrate an array comprising a series of at least two dilutions of each protein sample.

40. The method of claim 39, wherein analyzing the isolated protein sample for at least two cell populations further comprises:
applying a first labeled probe that specifically detects a first protein analyte; and
obtaining a quantitative value for the first protein analyte by comparing a signal from the first labeled probe at different positions in each of the dilution series.

41. The method of claim 40, further comprising:
applying a second labeled probe that specifically detects a second protein analyte; and
obtaining a quantitative value for the second protein analyte by comparing a signal from the second labeled probe at different positions in each of the dilution series.

42. The method of claim 18, wherein calibrating the assay comprises generating a serial dilution of the protein sample.

43. The method of claim 32 wherein the cellular component is immobilized.

44. The method of claim 29, wherein the confined zone is a microspot on a microarray.

45. The method of claim 1, wherein the isolated protein sample is referred to as a first isolated protein sample, and the method further comprises:

extracting a second population of about 1500 or fewer cells from the tissue sample or a second tissue sample;

isolating a second protein sample from the second extracted cell population; and analyzing the second isolated protein sample concurrently with the first isolated protein sample.

46. The method of claim 45, wherein the protein contents of more than two populations of cells are analyzed.

47. The method of claim 46, wherein the more than two populations of cells are extracted from more than two tissue samples.

48. The method of claim 46, wherein the more than two populations of cells are extracted from:
tissues from different stages of malignancy;
tissues before and after a treatment;
tissues from different stages of development of an embryo; or
combinations thereof.

49. A method comprising:
extracting more than one population of about 1500 or fewer cells from at least one tissue sample(s) under microscopic visualization;
isolating a protein sample from each of the extracted cell populations, wherein isolating the protein sample comprises solubilizing contents of the extracted cell populations in less than about 20 $\mu$l of a buffer; and
analyzing the isolated protein samples.

50. The method of claim 49, wherein the cells are extracted from more than one tissue sample.

51. The method of claim 50, wherein the more than one tissue samples are from a single subject.

52. The method of claim 49, wherein extracting the more than one population of cells from the tissue samples comprises using microdissection.

53. The method of claim 52, wherein the microdissection comprises laser capture microdissection.

54. The method of claim 49, wherein the more than one population of cells extracted from the tissue sample(s) is cultured in vitro prior to the step of isolating the protein sample from each of the cell populations.

55. The method of claim 54, wherein the more than one populations of cells are extracted from:
tissues from different stages of malignancy;
tissues before and after a treatment;
tissues from different stages of development of an embryo; or
combinations thereof.

56. The method of claim 49, wherein isolating the protein sample from each of the extracted cell populations comprises:
lysing the extracted cell populations to produce cellular components;
and wherein analyzing the isolated protein sample from each of the extracted cell populations comprises:
immobilizing at least one cellular component or a binding agent in a confined zone;
contacting the cellular components with a binding agent; and
detecting the interaction between the components and the binding agent.

57. The method of claim 56 wherein the cellular component is immobilized.

58. The method of claim 57 wherein the confined zone of the immobilized cellular component or the immobilized binding agent is an array.

59. The method of claim 56, wherein the confined zone is a microspot on a microarray.

60. The method of claim 1 wherein analyzing the isolated protein comprises performing an immunoassay using a labeled antibody specific for a protein of interest, wherein the assay is calibrated to indicate the amount of the protein of interest present in the sample.

61. The method of claim 60, wherein calibrating the assay comprises generating a serial dilution of the protein sample.

62. The method of claim 29 wherein analyzing the isolated protein further comprises using a calibration to indicate the amount of the protein of interest present in the sample.

63. The method of claim 62, wherein the calibration comprises generating a serial dilution of the protein sample.

64. The method of claim 35, wherein analyzing the isolated protein sample further comprises generating on the substrate of the array a protein standard comprising a series of at least two dilutions of at least one purified protein.

65. The method of claim 64, further comprising quantifying at least one protein in the protein sample, where the amount of protein is quantified in units relative to the amount of purified protein in the protein standard on the array.

66. The method of claim 64, where the protein standard comprises a mixture of two or more purified proteins, and wherein each of the two or more purified proteins is used to calibrate quantification of at least one cellular component in at least one protein sample on the array.

67. The method of claim 35, wherein each dilution is immobilized within a confined zone that can receive an individual reagent treatment.

68. The method of claim 49, wherein analyzing the isolated protein sample comprises generating on a substrate an array comprising a series of at least two dilutions of the protein sample.

69. The method of claim 68, wherein analyzing the isolated protein sample further comprises generating on the substrate of the array a protein standard comprising a series of at least two dilutions of at least one purified protein.

70. The method of claim 69, further comprising quantifying at least one protein in the protein sample, where the amount of protein is quantified in units relative to the amount of purified protein in the protein standard on the array.

71. The method of claim 69, where the protein standard comprises a mixture of two or more purified proteins, wherein each of the two or more purified proteins is used to calibrate quantification of at least one cellular component in at least one protein sample on the array.

72. The method of claim 68, wherein each dilution is immobilized within a confined zone that can receive an individual reagent treatment.

73. A method comprising:
extracting a population of about 1500 or fewer cells from a tissue sample;
isolating a protein sample from the extracted cell population, wherein isolating the protein sample from the extracted cell population comprises lysing the extracted cell population in less than about 20 $\mu$l of a buffer to produce cellular components; and
analyzing the isolated protein sample, wherein analyzing the isolated protein sample comprises:
generating on a substrate an array comprising a series of at least two dilutions of the protein sample;
contacting the array with a binding agent; and
detecting the interaction between the cellular components in the protein sample and the binding agent.

74. The method of claim 1, wherein extracting the population of cells using microdissection under microscopic visualization comprises:
- contacting the tissue sample with a transfer film;
- focally activating the transfer film with a laser beam, thereby bonding the cells to the transfer film; and
- lifting the bonded cells from the tissue sample, thereby extracting the population of cells and leaving unwanted cells behind.

75. A method comprising:
- contacting a tissue sample with a transfer film;
- microscopically visualizing a population of cells in the tissue sample;
- focally activating the transfer film with a laser beam, thereby bonding the population of cells to the transfer film;
- extracting the population of cells from the tissue sample, thereby leaving unwanted cells behind, to produce an extracted cell population of about 1500 or fewer cells;
- isolating a protein sample from the extracted cell population, wherein isolating the protein sample comprises solubilizing contents of the extracted cell population in less than about 20 µl of a buffer; and
- analyzing the isolated protein sample.

76. The method of claim 75, wherein the buffer comprising at least one detergent to solubilize the cellular lipids, at least one proteinase inhibitor to preserve protein content and function, and at least one salt to lyse the nuclear contents.

77. The method of claim 76 wherein the cell contents are solubilized in about 1 µl to about 15 µl of buffer.

* * * * *